(12) United States Patent
Uchida

(10) Patent No.: US 9,310,345 B2
(45) Date of Patent: Apr. 12, 2016

(54) SENSOR SYSTEM, COMPUTER, AND MACHINE

(75) Inventor: Takayuki Uchida, Hitachi (JP)

(73) Assignee: HITACHI, LTD., Tokyo (JP)

( * ) Notice: Subject to any disclaimer, the term of this patent is extended or adjusted under 35 U.S.C. 154(b) by 572 days.

(21) Appl. No.: 13/817,924

(22) PCT Filed: Sep. 30, 2010

(86) PCT No.: PCT/JP2010/067164
§ 371 (c)(1),
(2), (4) Date: Feb. 20, 2013

(87) PCT Pub. No.: WO2012/042649
PCT Pub. Date: Apr. 5, 2012

(65) Prior Publication Data
US 2013/0151170 A1     Jun. 13, 2013

(51) Int. Cl.
*G01N 33/00*    (2006.01)
*G06F 15/00*    (2006.01)
*G06Q 10/06*    (2012.01)

(52) U.S. Cl.
CPC ............. *G01N 33/00* (2013.01); *G06F 15/00* (2013.01); *G06Q 10/06* (2013.01)

(58) Field of Classification Search
CPC ........ G01N 33/00; G06F 15/00; G06Q 10/06; G06Q 10/0633; E02F 9/26; E02F 9/267; G05B 23/0272

USPC .......................... 702/33, 183, 184, 185, 188; 342/357.75; 701/1, 29.1, 33, 50; 705/7.27

See application file for complete search history.

(56) References Cited

U.S. PATENT DOCUMENTS

| | | | | |
|---|---|---|---|---|
| 6,728,619 | B2 * | 4/2004 | Sugiyama | ................. E02F 9/26 342/357.75 |
| 7,222,051 | B2 * | 5/2007 | Shibata | ................... E02F 9/205 701/1 |
| 2008/0140435 | A1 | 6/2008 | Arakawa | |

FOREIGN PATENT DOCUMENTS

| | | |
|---|---|---|
| JP | 2008-009935 | 1/2008 |
| JP | 2009-003561 | 1/2009 |
| WO | WO 2006/085469 A1 | 8/2006 |

* cited by examiner

*Primary Examiner* — John H Le
(74) *Attorney, Agent, or Firm* — Baker Botts L.L.P.

(57) ABSTRACT

A machine in a sensor system is configured to measure conditions of parts in the machine with sensors, collect pieces of sensor data generated by the measurements, and transmit the collected pieces of sensor data to a computer while connecting to the computer via a network. The computer in the sensor system is configured to create an index for indicating that the machine is in a predetermined condition, based on the transmitted pieces of sensor data, and transmit the created index to the machine. The machine is configured to diagnose whether the machine is in the predetermined condition with the transmitted index and collected pieces of sensor data.

8 Claims, 22 Drawing Sheets

| | 4431 | 4430 | |
|---|---|---|---|
| | MODEL 0101 | | |
| 4433 | CENTER OF NORMAL RANGE | RADIUS OF NORMAL RANGE | 4436 |
| | (X11,Y11),(X12,Y12),... | R11,R12,... | |

*FIG. 8*

| MACHINE ID (4610) | TABLE NAME (4630) | SENSOR NAME LIST (4650) |
|---|---|---|
| 00000 | STBL00000 | SENSOR 1,2,···,N |
| 00001 | STBL00001 | SENSOR 1,2,···,M |
| 00002 | STBL00002 | SENSOR 1,2,···,L |
| : | : | : |

*FIG. 11*

3710 points to SENSOR NAME LIST column.

| STBL00000 | | | | | |
|---|---|---|---|---|---|
| ACQUISITION TIME (4920) | SENSOR 1 (4930-1) | SENSOR 2 (4930-2) | SENSOR 3 (4930-3) | ·· | SENSOR N (4930-N) |
| 2010/01/20 00:00:00 | 1.0001 | 2.5679 | 235.02 | ·· | 23.983 |
| 2010/01/21 00:00:01 | 1.0000 | 2.0010 | 1045.0 | ·· | 12.010 |
| : | : | : | : | : | : |

| STBL00001 | | | | | |
|---|---|---|---|---|---|
| ACQUISITION TIME | SENSOR 1 | SENSOR 2 | SENSOR 3 | ·· | SENSOR M |
| 2010/01/20 00:00:00 | 1.2356 | 5.9000 | 539.32 | ·· | 92.354 |
| 2010/01/21 00:00:01 | 1.0230 | 6.7010 | 2390.0 | ·· | 35.620 |
| : | : | : | : | : | : |

| STBL00002 | | | | | |
|---|---|---|---|---|---|
| ACQUISITION TIME | SENSOR 1 | SENSOR 2 | SENSOR 3 | ·· | SENSOR L |
| 2010/01/20 00:00:00 | 1.5356 | 5.3259 | 290.32 | ·· | 34.554 |
| 2010/01/21 00:00:01 | 1.5203 | 2.7010 | 239.03 | ·· | 18.620 |
| : | : | : | : | : | : |

*FIG. 12*

| | 5410 | 5440 3720 |
|---|---|---|
| | MACHINE ID | DIAGNOSIS MODEL FRAGMENT TABLE NAME |
| | 00000 | MTBL00000 |
| | 00001 | MTBL00001 |
| | 00002 | MTBL00002 |
| | : | : |

| MTBL00000 | |
|---|---|
| ORIGINAL DATA ACQUISITION DATE | DIAGNOSIS MODEL FRAGMENT |
| 2010/01/20 | MODEL 00000_0101 |
| 2010/01/21 | MODEL 00000_0102 |
| : | : |

| MTBL00001 | |
|---|---|
| ORIGINAL DATA ACQUISITION DATE | DIAGNOSIS MODEL FRAGMENT |
| 2010/01/20 | MODEL 00001_0101 |
| 2010/01/21 | MODEL 00001_0102 |
| : | : |

| MTBL00002 | |
|---|---|
| ORIGINAL DATA ACQUISITION DATE | DIAGNOSIS MODEL FRAGMENT |
| 2010/01/20 | MODEL 00002_0101 |
| 2010/01/21 | MODEL 00002_0102 |
| : | : |

|  | 5641 | 5640 |
| --- | --- | --- |
| 5643 | MODEL 00000_0101 | |
| | CENTER OF NORMAL RANGE | RADIUS OF NORMAL RANGE | 5646 |
| | (X1,Y1) | R1 |
| | (X2,Y2) | R2 |
| | : | : |

FIG. 15

| 11150 | 11170 | 3750 |
| --- | --- | --- |
| MACHINE ID | WORKING DAY TABLE NAME | |
| 00000 | MDTBL00000 |
| 00001 | MDTBL00001 |
| 00002 | MDTBL00002 |
| : | : |

FIG. 16

| MDTBL00000 | |
|---|---|
| DATE | STATE |
| 2010/01/20 | WORKING DAY |
| 2010/01/21 | WORKING DAY |
| : | : |

| MDTBL00001 | |
|---|---|
| DATE | STATE |
| 2010/01/20 | NON-WORKING DAY |
| 2010/01/21 | NON-WORKING DAY |
| : | : |

| MDTBL00002 | |
|---|---|
| DATE | STATE |
| 2010/01/20 | NON-WORKING DAY |
| 2010/01/21 | WORKING DAY |
| : | : |

*FIG. 17*

| DIAGNOSIS DAY | CENTER OF NORMAL RANGE | RADIUS OF NORMAL RANGE |
|---|---|---|
| 2010/1/20 | (X11,Y11),(X12,Y12),... | R11,R12,... |
| 2010/1/21 | (X21,Y21),(X22,Y22),... | R21,R22,... |
| ⋮ | ⋮ | ⋮ |

*FIG. 25*

SENSOR SYSTEM, COMPUTER, AND MACHINE

BACKGROUND OF THE INVENTION

This invention relates to a sensor system, and particularly relates to a sensor system for examining sensor data.

When using a machine such as a gas engine, an elevator, a mining machine, or a construction machine, maintenance of the machine is essential to keep it working. For effective maintenance of the machine, techniques have been proposed that examine the machine for any abnormality to detect a sign of failure and provide the controller with a means to eliminate the failure.

There exists a technique, in which sensors installed in a machine measure the condition of the machine and sends the measured data (hereinafter, referred to as sensor data) to a data center via a communications line, and the data center that has received the sensor data examines the received sensor data to detect a sign of failure in the machine (for example, refer to Patent Literature 1, JP2009-003561A).

There exists another technique, in which a machine prepares, in the machine, a model to detect a sign of failure from sensor data using unsupervised learning in a neural network and detects a sign of failure based on the prepared model and sensor data on the machine (for example, refer to Patent Literature 2, JP 2008-009935A).

SUMMARY OF THE INVENTION

A machine such as a heavy mining machine that works at a remote place is used at a place distant from a communications line to communicate with a data center; accordingly, it cannot always connect to the data center. Consequently, the machine working at a remote place cannot send sensor data to the data center every time sensors generate sensor data by measurement by the sensors.

When the technique disclosed in Patent Literature 1 is applied to such a machine working at a remote place, sensor data measured in the machine is not sent to the data center until the machine communicates with the data center, so that detection of a sign of failure is delayed.

On the other hand, when the technique disclosed in Patent Literature 2 is applied to the aforementioned machine working at a remote place, a sign of failure is detected inside the machine; accordingly, the sign of failure is instantly detected at the remote place where the machine is not connected to the data center.

To detect a failure with high accuracy, however, it is necessary to analyze a huge amount of sensor data, create a diagnosis model before examination, and make examination for any failure with the created diagnosis model. In the meanwhile, the condition of the machine changes because of aging and seasonally varying temperature and humidity; accordingly, the created diagnosis model should be updated in a short cycle in accordance with the change in temperature, humidity, and the like. For short-cycle updates of a diagnosis model required to detect an abnormality in the machine, massive computer resources are required that enable a huge amount of sensor data to be processed at high speed.

If computer resources included in a machine working at a remote place are limited, there arises a problem that creating a highly accurate diagnosis model, like the one created in a technique disclosed in Patent Literature 2, is difficult for the machine.

This invention aims to accurately diagnose whether a machine not allowed to send/receive data over a communications line all the time, such as a heavy construction or mining machine working at a remote place, is abnormal, and to report the diagnosis to the maintenance service company as soon as possible.

An representative example of this invention is a sensor system including a machine including sensors and a computer connected to the machine via a network. The machine is configured to measure conditions of parts in the machine with the sensors, collect pieces of sensor data generated by the measurements, and transmit the collected pieces of sensor data to the computer while connecting to the computer via the network. The computer is configured to create an index for indicating that the machine is in a predetermined condition, based on the transmitted pieces of sensor data, and transmit the created index to the machine. The machine is configured to diagnose whether the machine is in the predetermined condition with the transmitted index and collected pieces of sensor data.

An embodiment of this invention provides an accurate diagnosis whether a machine working at a site that cannot connect to a communications line is abnormal or not.

BRIEF DESCRIPTION OF THE DRAWINGS

FIG. 8 is an explanatory diagram illustrating a diagnosis model in the embodiment;

FIG. 11 is an explanatory diagram illustrating a machine sensor configuration table held in the data center in the embodiment;

FIG. 12 is an explanatory diagram illustrating center's collected sensor tables held in the data center in the embodiment;

FIG. 13 is an explanatory diagram illustrating a machine diagnosis configuration table held in the data center in the embodiment;

FIG. 14 is an explanatory diagram illustrating center's collected diagnosis model fragment tables held in the data center in the embodiment;

FIG. 15 is an explanatory diagram illustrating a diagnosis model fragment in the embodiment;

FIG. 16 is an explanatory diagram illustrating a machine working day configuration table held in the data center in the embodiment;

FIG. 17 is an explanatory diagram illustrating collected working day tables held in the data center in the embodiment;

FIG. 25 is an explanatory diagram illustrating a table for holding diagnosis models in a RAM in the embodiment.

DETAILED DESCRIPTION OF THE EMBODIMENTS

Hereinafter, an embodiment of this invention is described with reference to the drawings.

Figure 1:
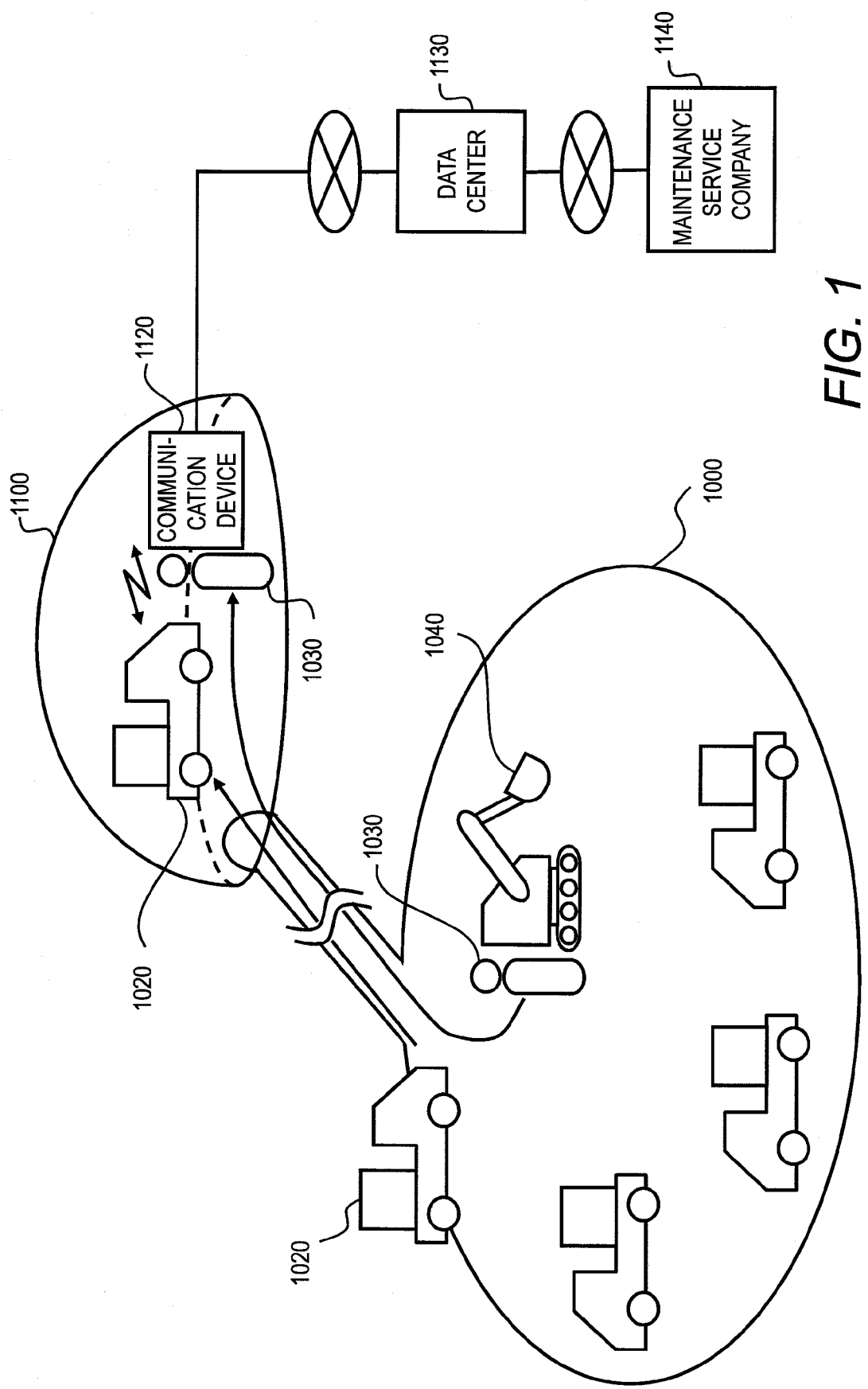
FIG. 1 is an explanatory diagram illustrating an operating environment for a system in an embodiment of this invention.

FIG. 1 is an explanatory diagram illustrating an operating environment for a system in this embodiment.

The system of this embodiment illustrated in FIG. 1 is installed in an environment including a working site 1000, a communication point 1100, a data center 1130, and a maintenance service company 1140. A machine 1020 and a machine 1040 in FIG. 1 are the machines to be maintained in this embodiment.

The working site 1000 is a place where the machine 1020 to be maintained in this embodiment works. The working site 1000 is a remote place like a mine and is a place difficult to connect to the data center 1130.

The machine 1020 and the machine 1040 work at the working site 1000. The machine 1020 may be a mining machine such as a truck, an excavator, or a loader. The machine 1020 can move from the working site 1000 and the machine 1040 is difficult to move from the working site 1000.

The communication point 1100 is a place equipped with facilities to communicate with the data center 1130, like an office or a garage. The communication point 1100 is distant from the working site 1000.

The communication point 1100 is equipped with a communication device 1120 to communicate with the data center 1130. The machine 1020 moves from the working site 1000 to the communication point 1100 and sends sensor data indicating the condition of the machine 1020 to the data center 1130 through the communication device 1120. The machine 1020 also receives a diagnosis model to be used to detect a sign of failure from the data center 1130.

To maintain the machine 1040 that cannot move from the working site 1000, the maintenance worker 1030 obtains a storage medium holding sensor data from the machine 1040 and takes the obtained storage medium to the communication point 1100. The maintenance worker 1030 sends the sensor data held in the storage medium to the data center 1130 through the communication device 1120.

The maintenance worker 1030 also stores a diagnosis model received from the data center 1130 in a storage medium and brings the storage medium holding the diagnosis model to the machine 1040. The maintenance worker 1030 connects the storage medium holding the diagnosis model to the machine 1040 for the machine 1040 to acquire the latest diagnosis model.

The data center is equipped with a computer having a high processing capability. It analyzes a huge amount of sensor data sent through the communication device 1120 and creates a diagnosis model to make examination for any abnormality or sign of failure in the machine 1020 or the machine 1040.

The maintenance service company 1140 is a company to maintain the machine 1020 and the machine 1040; it receives a report from the data center 1130 when a sign of failure is detected in the machine 1020 or the machine 1040.

The machine 1020 and the machine 1040 are both machines to be maintained. Accordingly, in the following description, the machine 1020 and the machine 1040 are generally referred to as examined machines 1010.

Figure 2:
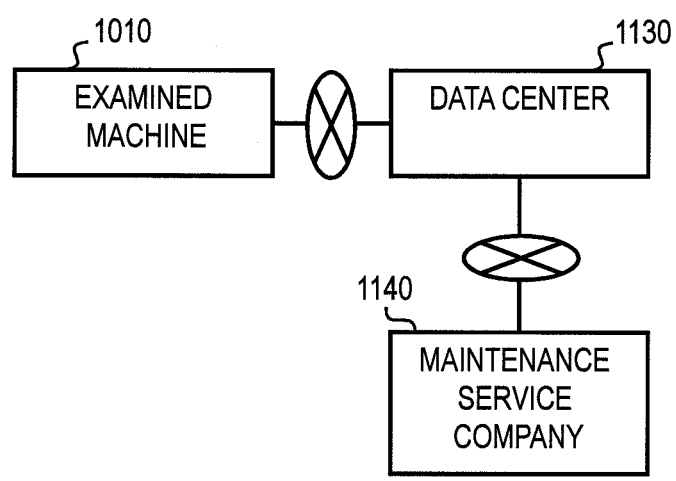
FIG. 2 is a block diagram illustrating a logical configuration of the system in the embodiment.

FIG. 2 is a block diagram illustrating a logical configuration of the system in this embodiment.

An examined machine 1010 is connected to the data center 1130 via a network. The maintenance service company 1140 is connected to the data center 1130 via a network.

Figure 3:
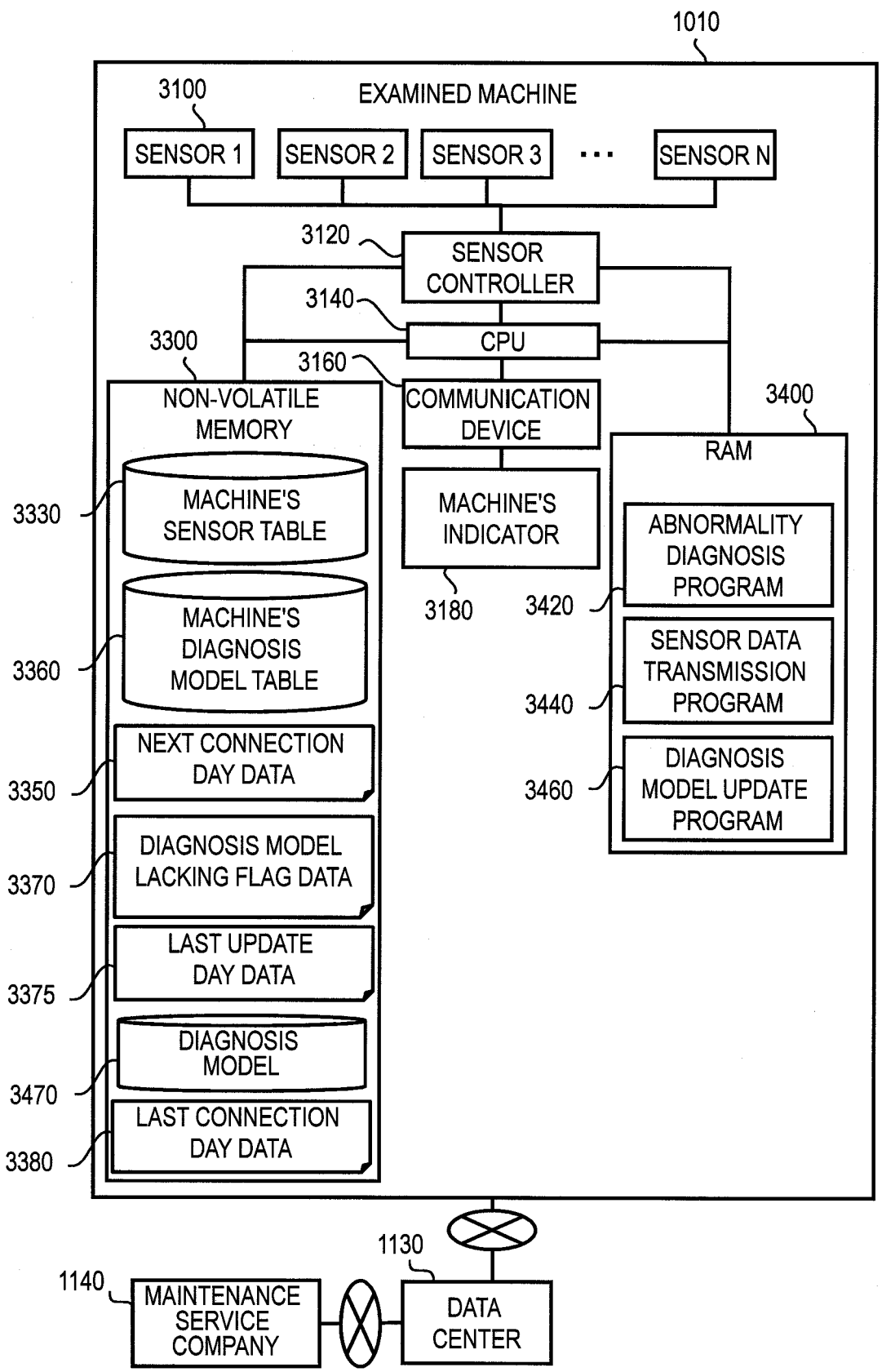
FIG. 3 is a block diagram illustrating a physical configuration of an examined machine in the embodiment.

FIG. 3 is a block diagram illustrating a physical configuration of the examined machine 1010 in this embodiment.

The examined machine 1010 includes sensors 3100 (3100-1 to 3100-N), a sensor controller 3120, a CPU 3140, a communication device 3160, a machine's indicator 3180, a non-volatile memory 3300, and a RAM 3400.

The sensors 3100 are sensors for measuring a physical value indicating the current condition of the examined machine 1010. The physical value of the examined machine 1010 is, for example, temperature, rotational frequency, or current of a built-in power generator.

The sensor controller 3120 collects sensor data from the sensors 3100. The sensor data is the data of results of measurement by the sensors 3100. The sensor controller 3120 stores the collected sensor data in the non-volatile memory 3300.

The CPU 3140 is a processor for executing programs stored in the RAM 3400. The communication device 3160 is a communication device for communicating data between the examined machine 1010 and the data center 1130.

The communication device 3160 is a device for connecting to the communication device 1120 at the communication point 1100. If the examined machine 1010 is the machine 1040, the communication device 3160 has a function to store sensor data in a storage medium such as a magnetic disk.

The machine's indicator 3180 is a device for indicating a detected abnormality or sign of failure to the operator of the examined machine 1010 upon detection of it. The machine's indicator 3180 may be a display or a device for generating sound.

The non-volatile memory 3300 is a storage medium, such as a flash memory, to hold stored information even if the examined machine 1010 is powered off. It stores sensor data, diagnosis models, and others. The non-volatile memory 3300 holds a machine's sensor table 3330, a machine's diagnosis model table 3360, next connection day data 3350, diagnosis model lacking flag data 3370, last update day data 3375, a diagnosis model 3470, and last connection day data 3380.

The machine's sensor table 3330 is a table for storing sensor data measured in the examined machine 1010. The machine's diagnosis model table 3360 is a table for storing the date of collection (or creation) of the diagnosis model stored in the diagnosis model 3470.

The next connection day data 3350 indicates the date for the examined machine 1010 to connect to the data center 1130 next. The diagnosis model lacking flag data 3370 stores a flag indicating whether the diagnosis model 3470 to be used to make examination for any abnormality or sign of failure in the examined machine 1010 is the latest version.

The last update day data 3375 indicates the date of the last update of the diagnosis model 3470 to be used in the examined machine 1010. The diagnosis model 3470 stores a diagnosis model to examine the machine 1010 for any abnormality. The last connection day data 3380 indicates the date of the last connection to the data center 1130.

The RAM 3400 is a high-speed readable/writable storage device, such as a DRAM or an SRAM, to hold programs to be executed by the CPU 3140. The RAM 3400 holds an abnormality diagnosis program 3420, a sensor data transmission program 3440, and a diagnosis model update program 3460.

The abnormality diagnosis program 3420 is a program to analyze sensor data after it is collected by the sensor controller 3120. This program diagnoses whether the examined machine 1010 is abnormal or not and further, diagnoses whether any sign of failure exists or not.

The sensor data transmission program 3440 is a program to send sensor data stored in the machine's sensor table 3330 to the data center 1130.

The diagnosis model update program 3460 is a program to acquire a diagnosis model stored in the machine's diagnosis model table 3360 and update the diagnosis model 3470 with it by loading the diagnosis model to the non-volatile memory 3300.

The diagnosis model 3470 is data to be used by the abnormality diagnosis program 3420 when the program 3420 examines the machine 1010 for any abnormality based on sensor data.

Figure 4:
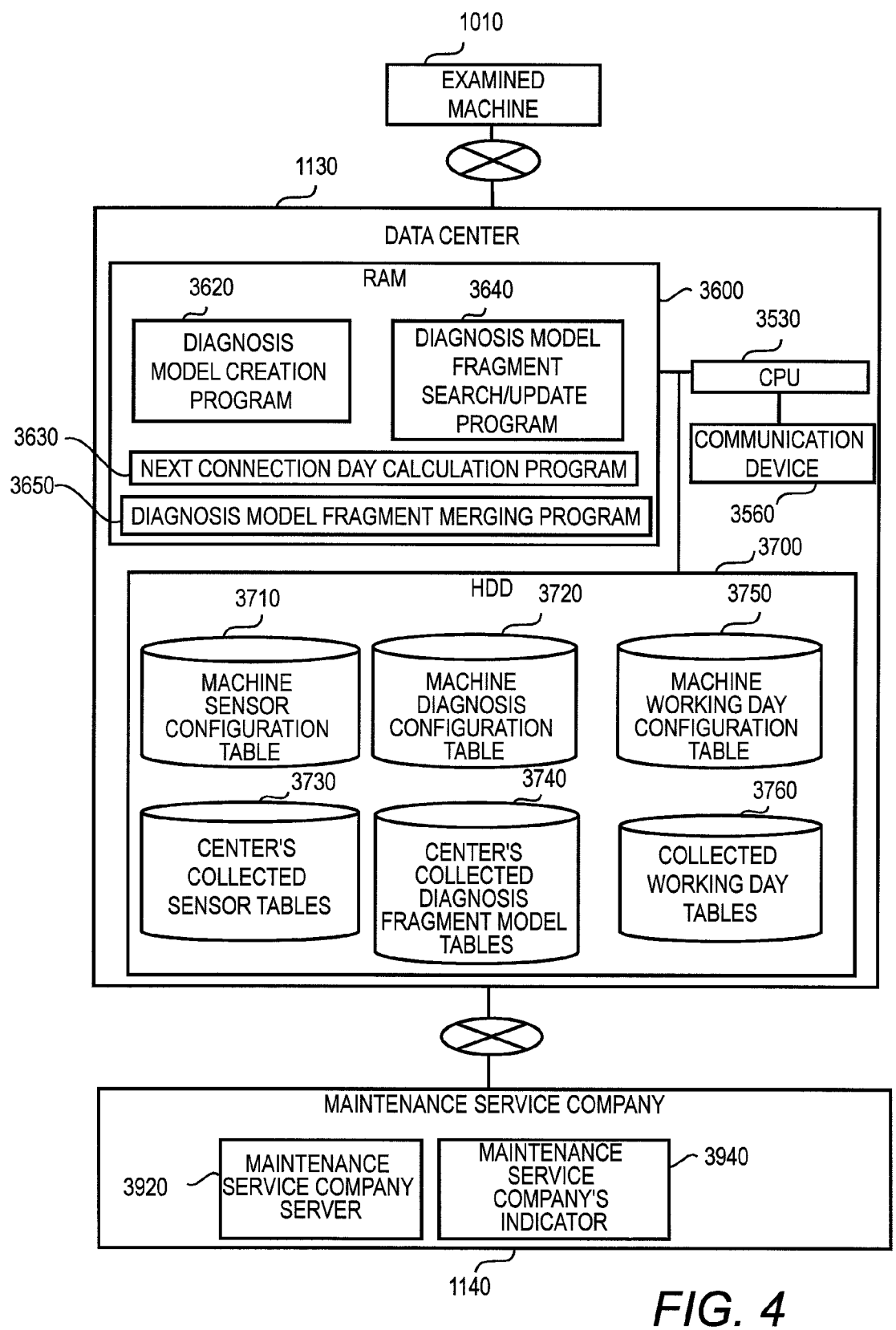
FIG. 4 is a block diagram illustrating physical configurations of a data center and a maintenance service company in the embodiment.

FIG. 4 is a block diagram illustrating physical configurations of the data center 1130 and the maintenance service company 1140 in this embodiment.

The data center 1130 includes a CPU 3530, a communication device 3560, a RAM 3600, and an HDD 3700.

The CPU 3530 is a processor to execute programs stored in the RAM 3600. The communication device 3560 is a device to communicate with the examined machine 1010.

The RAM 3600 is a high-speed readable/writable storage device, such as a DRAM or an SRAM. The RAM 3600 holds a diagnosis model creation program 3620, a diagnosis model fragment search/update program 3640, a next connection day calculation program 3630, and a diagnosis model fragment merging program 3650.

The diagnosis model creation program 3620 is a program to create a diagnosis model to be used in analyzing sensor data sent by the examined machine 1010 and examining the machine 1010 for any abnormality. The diagnosis model fragment search/update program 3640 is a program to search center's collected diagnosis model fragment tables 3740 for diagnosis model fragments required for the examined machine 1010 and to update diagnosis model fragments required for the examined machine 1010.

The next connection day calculation program 3630 is a program to calculate the date for the examined machine 1010 to connect to the data center 1130. The diagnosis model fragment merging program 3650 is a program to create a diagnosis model indicating a normal range of sensor data for several days (later-described learning days) by merging diagnosis model fragments.

The HDD 3700 is typically a large-capacity hard disk drive. It holds sensor data of all the examined machines 1010 working at the working site 1000 in FIG. 1 and data of diagnosis models for all of the examined machines 1010. The HDD 3700 holds a machine sensor configuration table 3710, a machine diagnosis configuration table 3720, a machine working day configuration table 3750, center's collected sensor tables 3730, center's collected diagnosis model fragment tables 3740, and collected working day tables 3760.

The machine sensor configuration table 3710 holds identifiers uniquely representing all the examined machines 1010 working at the working site 1000 and the names of tables for storing sensor data associated with the identifiers. The center's collected sensor tables 3730 are tables for holding sensor data measured in the examined machines 1010 on a machine-by-machine basis.

The machine diagnosis configuration table 3720 holds the identifiers of all the examined machines 1010 working at the working site 1000 and the names of tables for storing diagnosis models associated with the identifiers. The center's collected diagnosis model fragment tables 3740 are tables for holding diagnosis models for the examined machines 1010 on a machine-by-machine basis.

The machine working day configuration table 3750 holds the identifiers of all the examined machines 1010 working at the working site 1000 and the names of tables in the collected working day tables 3760 holding the working dates of the examined machines 1010 corresponding to the identifiers. The collected working day tables 3760 are tables for holding working days of the examined machines 1010 on a machine-by-machine basis.

The maintenance service company 1140 has a maintenance service company server 3920 and a maintenance service company's indicator 3940.

The maintenance service company server 3920 is a computer installed in the maintenance service company 1140. If examination by the data center 1130 results in detection of an abnormality or a sign of failure in a machine 1010 working at the working site 1000 in FIG. 1, the maintenance service company server 3920 receives a report of the abnormality from the data center 1130.

The maintenance service company's indicator 3940 is a device to notify the system administrator working for the maintenance service company 1140 of the report of the abnormality in the examined machine 1010 received by the maintenance service company server 3920. The maintenance service company's indicator 3940 includes a liquid crystal display, a cathode-ray tube display, or an audio indicator.

Figure 5:
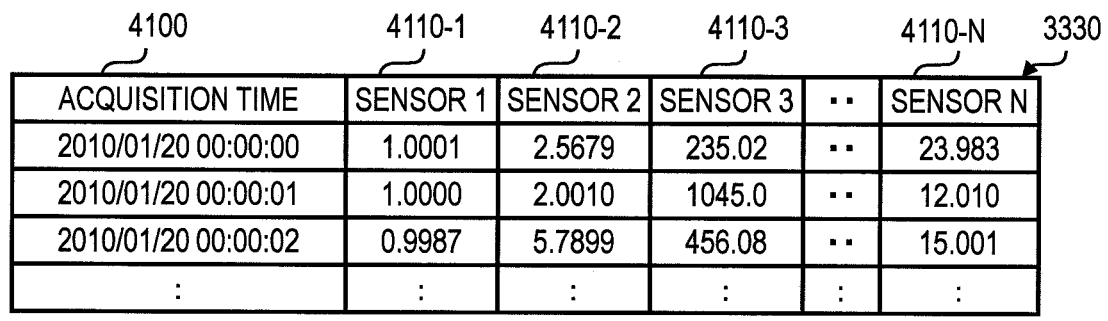
FIG. 5 is an explanatory diagram illustrating a machine's sensor table in the embodiment.

FIG. 5 is an explanatory diagram illustrating the machine's sensor table 3330 in this embodiment.

The machine's sensor table 3330 includes acquisition times 4100 and sensor data 4110 (4110-1 to 4110-N). A piece of sensor data 4110 (4110-1 to 4110-N) shows sensor data values collected from the sensors 3100 (3100-1 to 3100-N).

An acquisition time 4100 indicates the time at which sensor data 4110 (4110-1 to 4110-N) is collected from the sensors 3100 (3100-1 to 3100-N). The sensor controller 3120 collects sensor data either in a short cycle or in a cycle of measurement by the sensors 3100. Accordingly, the acquisition time 4100 is almost the same as the time at which the sensor data is generated by the sensors 3100.

With designation of an acquisition time 4100 in the machine's sensor table 3330, sensor data 4110 associated with the designated acquisition time 4100 can be obtained.

Figure 6:
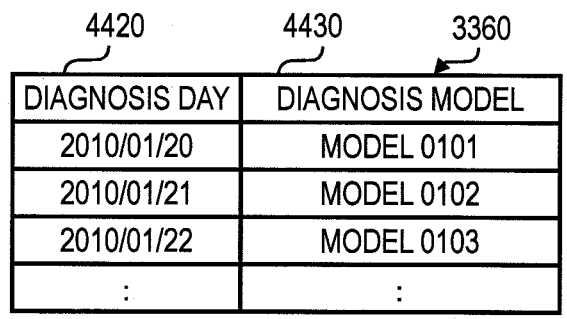
FIG. 6 is an explanatory diagram illustrating a machine's diagnosis model table in the embodiment.

FIG. 6 is an explanatory diagram illustrating the machine's diagnosis model table 3360 in this embodiment.

The machine's diagnosis model table 3360 includes diagnosis days 4420 and diagnosis models 4430. The diagnosis models 4430 are identifiers uniquely representing diagnosis models. The diagnosis days 4420 indicate dates to examine sensor data with diagnosis models represented by the diagnosis models 4430.

The diagnosis model in this embodiment is a model indicating a range for normal values for measured sensor data. With reference to FIG. 15, the diagnosis model and examination for any abnormality with the diagnosis model are described.

FIGS. 7A to 7E are explanatory diagrams illustrating distribution of sensor data and a diagnosis model in this embodiment.

Figure 7A:
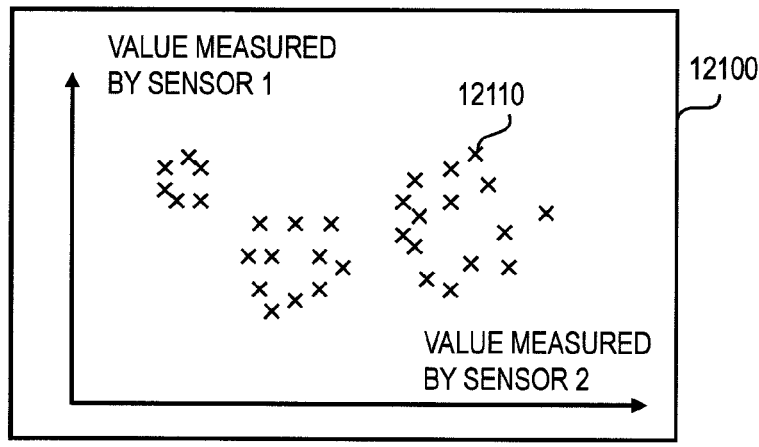
FIG. 7A is an explanatory diagram illustrating distribution of sensor data and a diagnosis model in the embodiment.

A model 12100 in FIG. 7A is distribution of sensor data for one day measured by sensors 3100-1 and 3100-2 included in an examined machine 1010 when the examined machine 1010 is working normally; in the model 12100, sensor data are arranged on a two-dimensional coordinate system depending on the time of collection (acquisition time 4100) of the sensor data. A point 12110 in FIG. 7A represents a piece of sensor data.

Figure 7B:
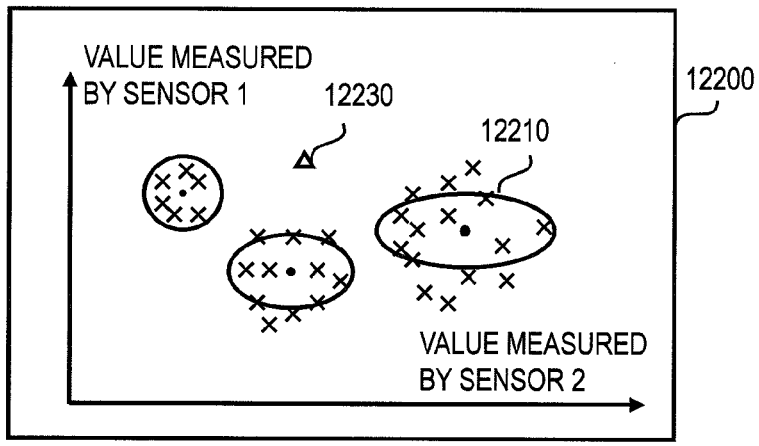
FIG. 7B is an explanatory diagram illustrating distribution of sensor data and a diagnosis model in the embodiment.

When a pattern of sensor data is learned from the distribution of sensor data represented by the model 12100 with a clustering technique, which is one of the machine learning techniques, distribution areas of normal sensor data are approximated into circular areas, like a circle 12210 in the model 12200 in FIG. 7B.

Figure 7C:
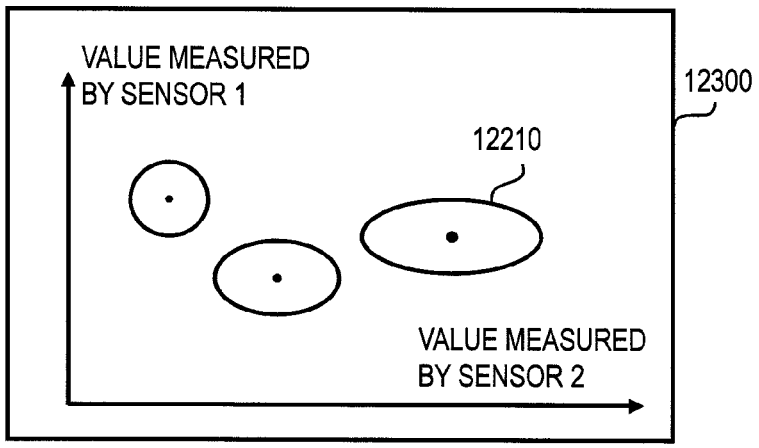
FIG. 7C is an explanatory diagram illustrating distribution of sensor data and a diagnosis model in the embodiment.

The model 12300 in FIG. 7C shows three circular areas in the case where all the distribution areas of sensor data in the model 12100 has been approximated into circular areas. The coordinates of the center and the radius of each approximated circular area are calculated.

If a piece of collected sensor data is included in the circular areas in the model 12300, it means that the examined machine 1010 in which the sensors 3100-1 and 3100-2 measure sensor data is normally working.

On the contrary, if the collected sensor data is off from the normal distribution areas of sensor data obtained by the above-described method, the examined machine 1010 in which the sensor data has been measured is diagnosed as abnormal. For example, if sensor data like a point 12230 included in the model 12200 is collected by the sensors 3100-1 and 3100-2, the examined machine 1010 in which the sensors 3100-1 and 3100-2 measure sensor data is diagnosed as abnormal.

Figure 7D:
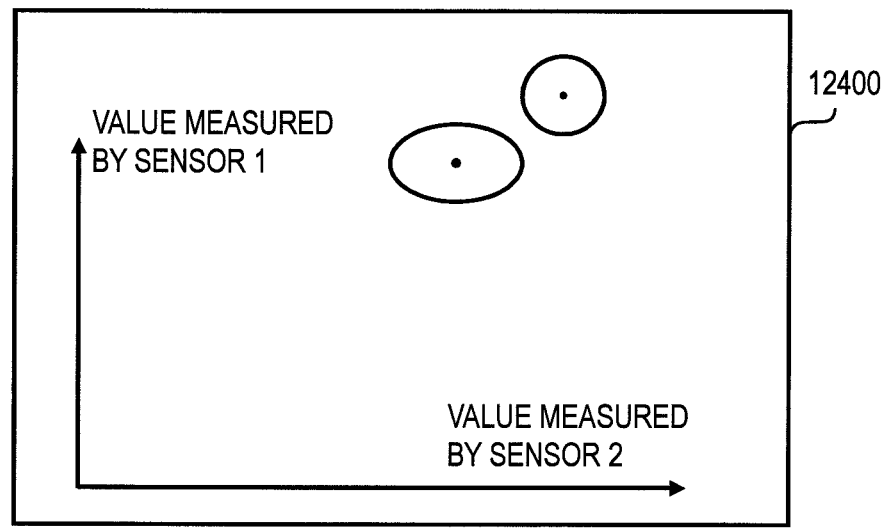
FIG. 7D is an explanatory diagram illustrating distribution of sensor data and a diagnosis model in the embodiment.

The model 12400 in FIG. 7D shows distribution areas of normal sensor data obtained as a result of learning sensor data measured on another day by the sensors 3100-1 and 3100-2 with the aforementioned clustering technique. By merging the models 12300 and 12400, a diagnosis model representing distribution of normal sensor data for two days is created.

Figure 7E:
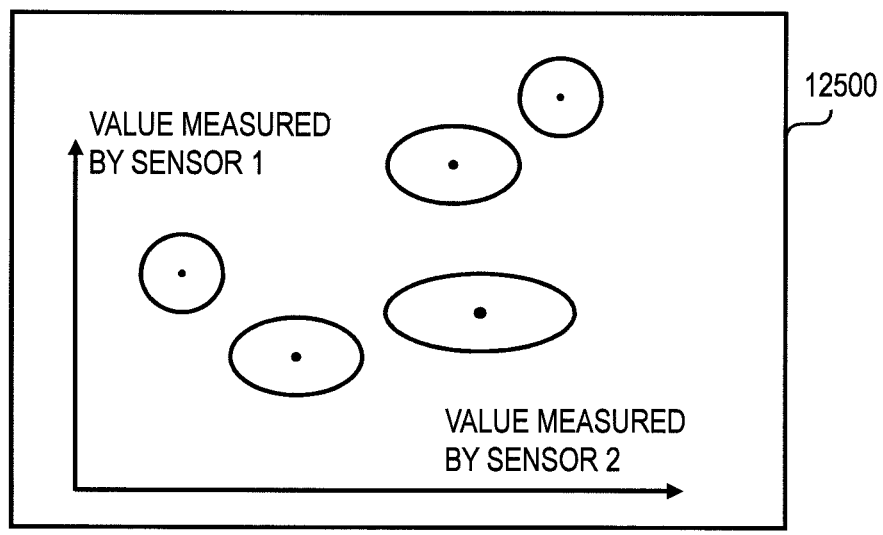
FIG. 7E is an explanatory diagram illustrating distribution of sensor data and a diagnosis model in the embodiment.

FIG. 7E shows a diagnosis model 12500 created by merging the models 12300 and 12400. To merge distribution areas of sensor data in this embodiment, a logical sum of the distribution areas is obtained.

Specifically, in creating a diagnosis model by merging distribution areas of sensor data, data of the coordinates of the centers and the radii of the approximated circular areas of the distribution areas in the models are added to create a diagnosis model.

In the following description, a model representing the distribution of normal sensor data generated in each day, like the model 12300, is referred to as a diagnosis model fragment. A model representing the distribution of normal sensor data for a plurality of days created by merging a plurality of diagnosis model fragments is referred to as a diagnosis model. In this embodiment, the diagnosis model is used to examine sensor data of a machine 1010.

FIG. 8 is an explanatory diagram illustrating a diagnosis model 4430 in this embodiment.

This diagnosis model 4430 is stored in the non-volatile storage memory 3300. The diagnosis model 4430 includes a diagnosis model ID 4431, the centers of normal ranges 4433, and the radii of normal ranges 4436.

The diagnosis model ID 4431 is an identifier for uniquely representing the diagnosis model and corresponds to the identifier stored in the diagnosis model 4430 in the machine's diagnosis model table 3360. The centers of normal ranges 4433 indicate the coordinates of the centers of the diagnosis model represented by the diagnosis model ID 4431. The radii of normal ranges 4436 indicate the radii of the diagnosis model represented by the diagnosis model ID 4431.

The method of examining sensor data by the machine 1010 in this embodiment creates a diagnosis model by learning sensor data collected before a diagnosis day 4420 and stores in advance the created diagnosis model in the diagnosis model 4430. On the day indicated by the diagnosis day 4420, the method examines sensor data using the diagnosis model associated with the diagnosis day 4420.

In this embodiment, days on which sensor data to be learned is generated in the examined machine 1010 are referred to as leaning days. The learning days include one or more days before the day to make a diagnosis. The number of days included in the learning days is predetermined by, for example, the administrator.

Since a diagnosis model is created from diagnosis model fragments of individual days included in the leaning days, the diagnosis model is created based on the condition of the examined machine 1010 during the learning days. The condition of the examined machine 1010 varies every day because of the surrounding environment, the aging of the machine, and others. For this reason, days closer to the diagnosis day should be selected as the leaning days.

Figure 9:
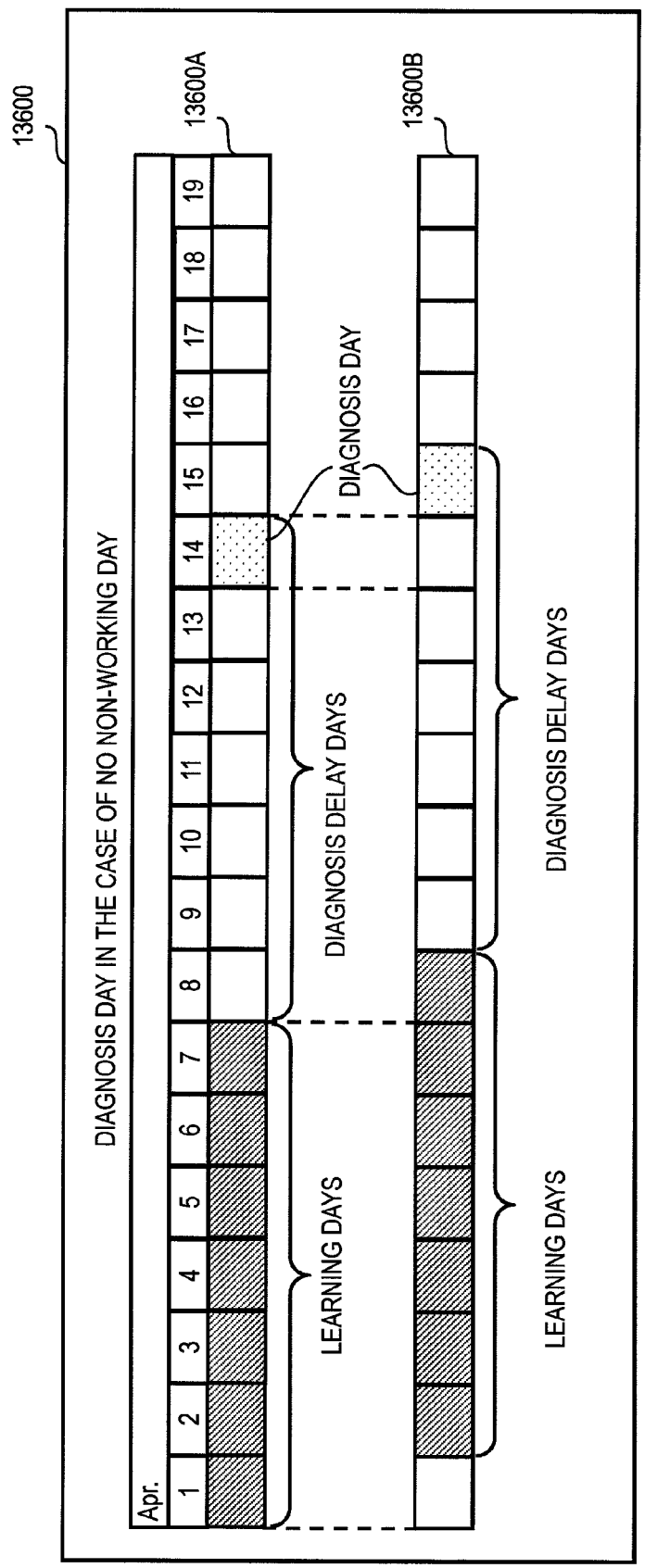
FIG. 9 is an explanatory diagram illustrating a diagnosis day and learning days in the embodiment in the case where the examined machine works on all the learning days.

FIG. 9 is an explanatory diagram illustrating the diagnosis day and the learning days in this embodiment in the case where the examined machine 1010 works on all the learning days.

A schedule 13600 shows the learning days, the diagnosis day, and diagnosis delay days in the case where the examined machine 1010 works on all the learning days. The schedule 13600 includes three examples: a schedule 13600A, a schedule 13600B, and a schedule 13600C.

Each cell in the schedule 13600 shows a date. The schedule 13600 shows each date of April 1 to April 19.

In the schedule 13600A, the learning days are April 1 to April 7. The diagnosis day is April 14, which is seven days later than April 7 or the last day of the learning days. The diagnosis delay days in this schedule 13600 are seven days. The days included in the learning days are also seven days.

The diagnosis delay days in this embodiment are the number of days after the last day of the learning days until the diagnosis day. The value for the diagnosis delay days is predetermined by the administrator.

The value for the diagnosis delay days depends on the environment of the working site 1000, the kind of the examined machine 1010, or the like. For this reason, through testing various diagnosis delay days, an optimum value leading to the most accurate abnormality diagnosis is determined for the diagnosis delay days.

In the meanwhile, every time the diagnosis day is shifted by one day, the learning days are also shifted by one day. The schedule 13600B shows the learning days and the diagnosis delay days in the case where the diagnosis day in the schedule 13600A is shifted later by one day. The diagnosis day in the schedule 13600B is April 15 and the learning days are April 2 to April 8. The learning days in the schedule 13660B are shifted later by one day together with the diagnosis day; the diagnosis delay days do not change.

The schedule 13600C shows the learning days and the diagnosis delay days 13640 in the case where the diagnosis day in the schedule 13600B is further shifted later by one day. The diagnosis day in the schedule 13600C is April 16 and the learning days are April 3 to April 9.

Figure 10:
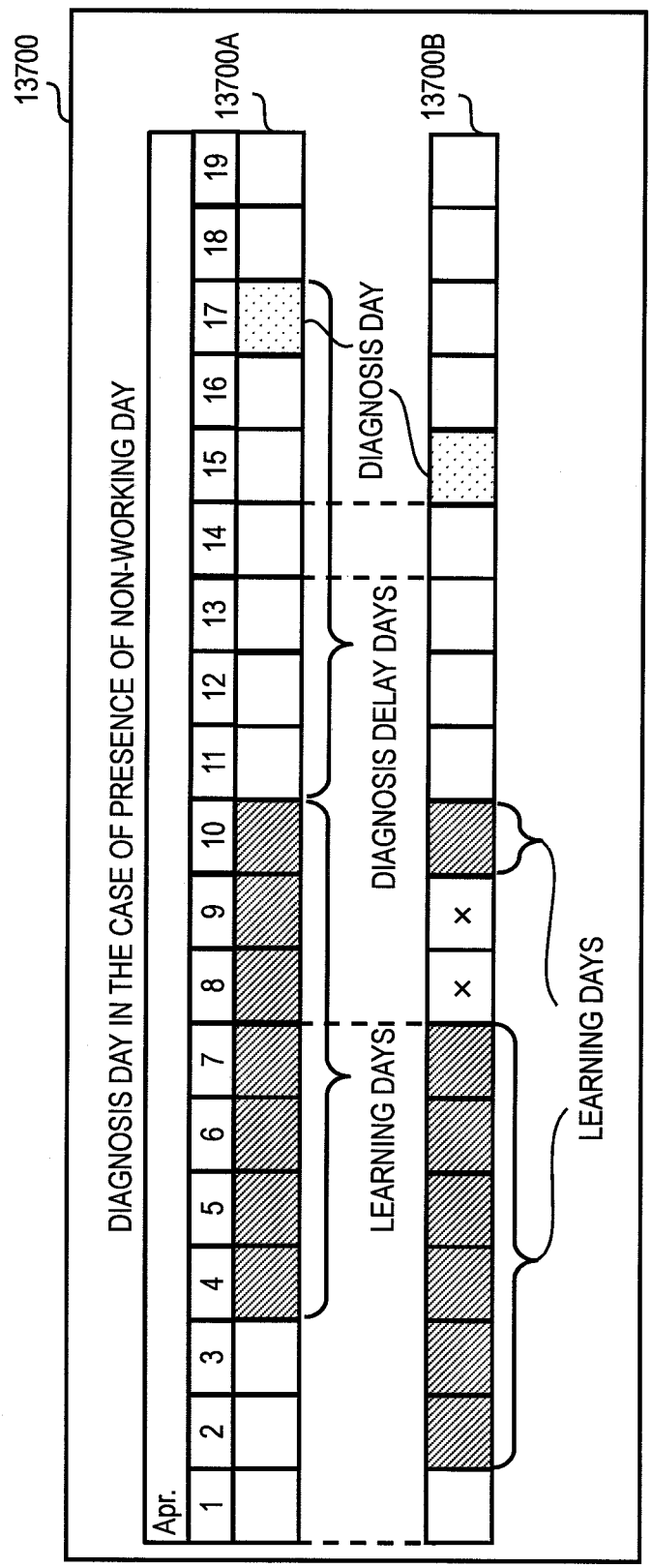
FIG. 10 is an explanatory diagram illustrating a diagnosis day and learning days in the embodiment in the case where the examined machine does not work on some of the learning days.

FIG. 10 is an explanatory diagram illustrating the diagnosis day and the learning days in this embodiment in the case where the examined machine 1010 does not work on some days.

A schedule 13700 includes two examples: a schedule 13700A and a schedule 13700B.

The schedule 13700A indicates the diagnosis day and the learning days in the case where the examined machine 1010 works on all the learning days. The learning days in the schedule 13700A are April 4 to April 10 and the diagnosis day is April 17.

The schedule 13700B is an example where the examined machine 1010 does not work for two days of the learning days in the schedule 13700A. On the days on which the examined machine 1010 does not work, sensor data is not collected in the examined machine 1010. The days on which the examined machine 1010 does not work (hereinafter referred to as non-working days) in the schedule 13700B are April 8 and April 9.

If the number of pieces of sensor data used for learning is reduced, the created diagnosis model becomes less accurate. Accordingly, if some non-working days exist, this embodiment extends the learning days backward by the number of days of the non-working days of the examined machine 1010. April 2 and April 3 in the schedule 13700B are the learning days extended backward, corresponding to the non-working days of April 8 and April 9.

However, in the case where the learning days are extended backward, the created diagnosis model reflects patterns of old sensor data strongly. Accordingly, the diagnosis day should be shifted backward together with the learning days.

In particular, as the non-working day is closer to the diagnosis day, the created diagnosis model strongly reflects the patterns of older sensor data, compared to the case of no non-working day. Accordingly, as the non-working day is closer to the diagnosis day, the diagnosis day should be shifted back more.

In view of the above, this embodiment calculates the number of days for the diagnosis day to be shifted back based on the average difference in days between each learning day and the diagnosis day. For example, the following formula (1) can be provided to calculate the average difference in days between each learning day and the diagnosis day:

Average difference in days={(date of diagnosis day−first date of learning days)+(date of diagnosis day−(first date of learning days+1))+(date of diagnosis day−(first date of learning days+2))+(date of diagnosis day−(first date of learning days+3))+0 . . . +(date of diagnosis day−last date of learning days)}/number of learning days (1)

The average difference in days between each learning day and the diagnosis day in the schedule 13700A is calculated as follows in accordance with the foregoing formula (1):

Average difference in days in the schedule 13700*A*:
{(17−4)+(17−5)+(17−6)+ . . . +(17−10)}/7=10 days In the schedule 13700B in the case where the learning days are April 2 to April 7 and April 10 and the diagnosis day is April 17, the average difference in days between each learning day and the diagnosis day is calculated as follows:

Average difference in days in the schedule 13700*B*:
{(17−2)+(17−3)+(17−4)+ . . . +(17−7)+(17−10)}/7=11.7 days The average difference in days in the case where the period of learning days includes non-working days is approximately two days longer than the average difference in days in the case where the period of learning days includes no non-working day. Accordingly, the diagnosis day in the schedule 13700A is shifted back by two days so that the diagnosis day is April 15 in the case of presence of non-working days. Through this operation, sensor data during the learning days is examined after the number of days equivalent to the predetermined optimum diagnosis delay days have passed. Consequently, this invention can prevent degradation in accuracy in the diagnosis model.

In the meanwhile, the examined machine 1010 in this embodiment requires everyday update of the diagnosis model. However, if the examined machine 1010 is connected to the data center 1130 every day, the expenses for operation and maintenance will increase. For this reason, the examined machine 1010 may not be connected to the data center 1130 every day.

Hence, on a connection day of the examined machine 1010 and the data center 1130, the data center 1130 needs to create diagnosis models for diagnosis days subsequent to the connection day, as many as possible, based on the sensor data to the connection day sent from the examined machine 1010. Then, the data center 1130 needs to send the created diagnosis models for several days to the examined machine 1010.

For example, the data center 1130 creates diagnosis models to be used in the cases where the diagnosis day is the day of the connection day+1 day, where the diagnosis day is the day of the connection day+2 days, . . . and where the diagnosis day is the day of the connection day+N days when it connects to the examined machine 1010.

The examined machine 1010 stores the diagnosis models sent from the data center 1130 in the machine's diagnosis model table 3360 of FIG. 6. Through this operation, even if the machine 1010 cannot connect to the data center 1130 every day, it can examine sensor data until all the diagnosis models 4430 stored in the machine's diagnosis model table 3360 are used up.

In this invention, the day on which the examined machine 1010 uses up all the diagnosis models created by the data center 1130 is determined to be the day of the next connection to the data center 1130. The examined machine 1010 receives new diagnosis models on the next connection day to prevent a diagnosis model from lacking in the examined machine 1010 at any time.

For example, in the cases where the examined machine 1010 is connected to the data center 1130 on April 10 in the schedules 13700A and 13700B in FIG. 10, the sensor data used for learning is sensor data collected in the examined machine 1010 by April 10.

In the schedule 13700A, the last day the machine 1010 can examine sensor data with the diagnosis models sent from the data center 1130 is April 17, which is after seven days of the diagnosis delay days. The next connection day should be April 18.

On the other hand, in the schedule 13700B, the last day the machine 1010 can examine sensor data with the diagnosis models sent from the data center 1130 is April 15, which is determined in consideration of the average difference in days between each learning day and the diagnosis day. The next connection day should be April 16.

It should be noted that, when the examined machine 1010 lacks a diagnosis model since it cannot connect to the data center 1130 by the next connection day, for example, because of an accident, "VALID" is stored in the diagnosis model lacking flag data 3370. If "VALID" is held in the diagnosis model lacking flag data 3370, sensor data is examined with an old diagnosis model.

If the machine 1010 diagnoses the machine 1010 itself as abnormal when "VALID" is held in the diagnosis model lacking flag data 3370, the diagnosis might be wrong because the applied diagnosis model is old. Accordingly, the data center 1130 makes a diagnosis again in accordance with later-described processing.

FIG. 11 is an explanatory diagram illustrating the machine sensor configuration table 3170 held in the data center 1130 in this embodiment.

The machine sensor configuration table 3710 includes machine IDs 4610, table names 4630, and sensor names 4650. The machine IDs 4610 are identifies uniquely representing examined machines 1010.

The table names 4630 are identifies representing tables for storing sensor data sent from the examined machines 1010 represented by the machine IDs 4610. The sensor names 4650 stores names uniquely representing sensors 3100 included in the examined machines 1010.

The machine sensor configuration table 3710 enables extraction of a sensor table holding sensor data with a machine ID from the center's collected sensor tables 3730.

FIG. 12 is an explanatory diagram illustrating the center's collected sensor tables 3730 held in the data center 1130 in this embodiment.

The center's collected sensor tables 3730 is a collection of tables each for storing sensor data sent from an examined machine 1010. The center's collected sensor tables 3730 include table names 4920, acquisition times 4925, and pieces of sensor data 4930 (4930-1 to 4930-N).

The table names 4920 are identifiers uniquely representing tables included in the center's collected sensor tables 3730. The table names 4920 correspond to the table names 4630 in the machine sensor configuration table 3710.

The acquisition times 4925 indicate the times at which the pieces of sensor data 4930 are collected from the sensors 3100, namely, the times of generation of the pieces of sensor data 4930. They correspond to the acquisition times 4100 in the machine's sensor table 3330 shown in FIG. 5.

The pieces of sensor data 4930 (4930-1 to 4930-N) indicate values of sensor data collected from the sensors 3100. Each piece of sensor data 4930 corresponds to each piece of sensor data 4110 in the machine's sensor table 3330 shown in FIG. 5.

To extract sensor data of an examined machine 1010, the data center 1130 extracts a table name 4630 associated with a machine ID 4610 in the machine sensor configuration table 3710 and extracts pieces of sensor data 4930 associated with the table name 4920 corresponding to the extracted table name 4630. At that time, it extracts pieces of sensor data based on the acquisition time 4925 of the sensor data 4930.

FIG. 13 is an explanatory diagram illustrating the machine diagnosis configuration table 3720 held in the data center 1130 in this embodiment.

The machine diagnosis configuration table 3720 includes machine IDs 5410 and diagnosis model fragment table names 5440. The machine IDs 5410 are identifiers uniquely representing examined machines 1010 and correspond to the machine IDs 4610 in the machine sensor configuration table 3710 shown in FIG. 11. The diagnosis model fragment table names 5440 are identifiers uniquely representing tables for storing diagnosis model fragments.

The data center 1130 can extract the identifier of a table included in the center's collected diagnosis model fragment tables 3740 with reference to the machine diagnosis configuration table 3720 with a machine ID 5410.

FIG. 14 is an explanatory diagram illustrating the center's collected diagnosis model fragment tables 3740 held in the data center 1130 in this embodiment.

The center's collected diagnosis model fragment tables 3740 are collected tables each for storing diagnosis model fragments. As previously described, each diagnosis model fragment is a day-by-day diagnosis model created by learning sensor data sent from an examined machine 1010.

Each table included in the center's collected diagnosis model fragment tables 3740 includes a diagnosis model fragment table name 5620, original data acquisition dates 5610, and diagnosis model fragments 5640. The diagnosis model fragment table name 5620 is an identifier uniquely representing a table for storing diagnosis model fragments. The diagnosis model fragment table name 5620 corresponds to a diagnosis model fragment table name 5440 in the machine diagnosis configuration table 3720 shown in FIG. 13.

Each original data acquisition date 5610 indicates the date on which sensor data used to create a diagnosis model fragment is collected from sensors 3100, namely the date of generation of the sensor data. The original data acquisition dates 5610 correspond to the acquisition times 4925 in the center's collected sensor tables 3730.

The diagnosis model fragments 5640 are identifiers uniquely representing diagnosis model fragments.

FIG. 15 is an explanatory diagram illustrating a diagnosis model fragment 5640 in this embodiment.

FIG. 15 illustrates a data structure of a diagnosis model fragment 5640, which is a result of learning from sensor data for one day.

The diagnosis model fragment 5640 includes a diagnosis model fragment ID 5641, centers of normal ranges 5643, and radii of normal ranges 5646. The diagnosis model fragment ID 5641 corresponds to the value stored in a diagnosis model fragment 5640 in the center's collected diagnosis model fragment tables 3740.

The centers of normal ranges 5643 are the coordinates of the centers of the normal ranges in the diagnosis model fragment 5640. The radii of normal ranges 5646 are the radii of the normal ranges in the diagnosis model fragment 5640.

The data center 1130 extracts diagnosis model fragments 5640 for several days with original data acquisition dates 5610. The data center 1130 merges the extracted diagnosis model fragments 5640 for several days to create a diagnosis model including normal ranges for several days.

FIG. 16 is an explanatory diagram illustrating the machine working day configuration table 3750 held in the data center 1130 in this embodiment.

The machine working day configuration table 3750 includes machine IDs 11150 and working day table names 11170. The machine IDs 11150 are identifiers uniquely representing examined machines 1010 and correspond to the machine IDs 5410 and the machine IDs 4610.

The working day table names 11170 are identifiers uniquely representing tables for storing information indicating working days of the examined machines 1010. The data center 1130 can extract the identifier of the table holding information on the days an examined machine 1010 works with a machine ID 11150.

FIG. 17 is an explanatory diagram illustrating the collected working day tables 3760 held in the data center 1130 in this embodiment.

The collected working day tables 3760 indicate whether individual examined machines 1010 work or do not work because of, for example, a holiday, on a day-by-day basis.

Each table included in the collected working day tables 3760 includes a working day table name 11500, dates 11700, and states 11600. The working day table name 11150 is an identifier uniquely representing the table for storing information on working days of an examined machine 1010. The working day table name 11500 corresponds to a working day table name 11170 in the machine working day configuration table 3750. The dates 11700 store dates day by day.

A state 11600 indicates whether an examined machine 1010 works on the date 11700. In this embodiment, if the examined machine 1010 works, the state 11600 indicates "WORKING DAY"; otherwise if it does not work, the state 11600 indicates "NON-WORKING DAY".

The states 11600 in the collected working day tables 3760 may have values stored in advance by a maintenance worker in accordance with the working schedules of the examined machines 1010.

The collected working day tables 3760 are separated into tables by examined machine 1010. The data center 1130 can extract the states 11600 of the individual examined machines 1010 with a date 11700.

Figure 18:
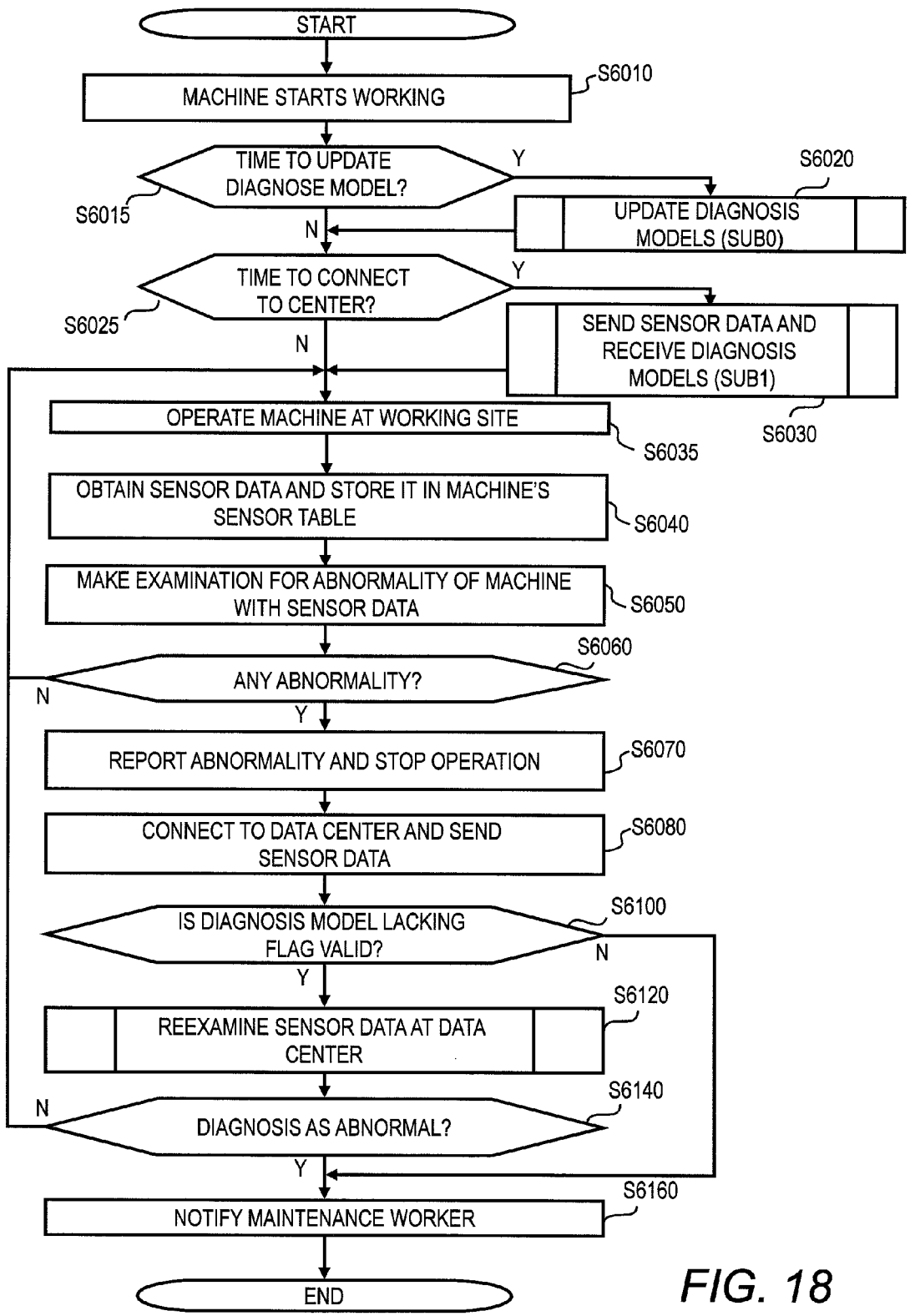
FIG. 18 is a flowchart illustrating overall processing in the embodiment.

FIG. 18 is a flowchart illustrating overall processing in this embodiment.

First, an examined machine 1010 starts to work (S6010). Specifically, if the examined machine 1010 is a movable machine 1020 such as a truck or an excavator, it means a worker turns on an engine switch. If the examined machine 1010 is a stationary machine 1040 such as a power generator, it means a worker turns on a power switch.

After S6010, the examined machine 1010 determines whether the current day is one or more days after the date of the last update of the diagnosis model. Specifically, it refers to the last update day data 3375 shown in FIG. 3 and determines whether the current date in the examined machine 1010 is one or more days later than the last update day data 3375 that is referred to (S6015). The examined machine 1010 has a function to acquire the current date during operation.

If one or more days have passed since the date of the last update day data 3375, the current day is a day to update the diagnosis model; the examined machine 1010 proceeds to S6020. If less than one day has passed since the last update day data 3375, it is not necessary to update the diagnosis model; the examined machine 1010 proceeds to S6025.

The examined machine 1010 updates the diagnosis model in the examined machine 1010 each day in accordance with S6015.

At S6020, the examined machine 1010 updates the diagnosis model in accordance with a subroutine SUB0 described below.

Figure 19:
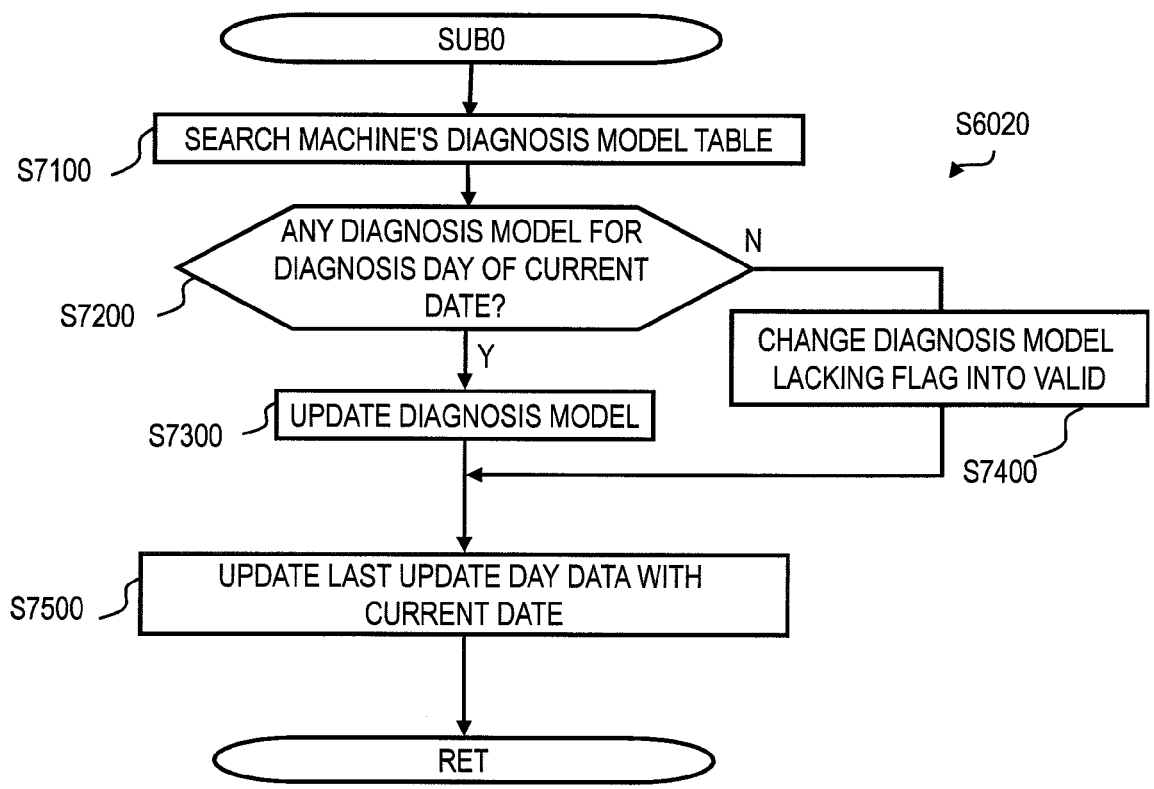
FIG. 19 is a flowchart illustrating processing of a subroutine SUB0 in the embodiment.

FIG. 19 is a flowchart illustrating processing of the subroutine SUB0 in this embodiment.

After S6015, the diagnosis model update program 3460 refers to the machine's diagnosis model table 3360 and extracts a diagnosis model 4430 for the diagnosis day 4420 of the current date (S7100).

After S7100, the diagnosis model update program 3460 determines whether a diagnosis model 4430 for the diagnosis day 4420 of the current date has been extracted as a result of S7100 (S7200).

If a diagnosis model 4430 for the diagnosis day 4420 of the current date has been extracted, the diagnosis model update program 3460 proceeds to S7300. If a diagnosis model 4430 for the diagnosis day 4420 of the current date cannot be extracted, the diagnosis model update program 3460 proceeds to S7400.

At S7300, the diagnosis model update program 3460 loads the diagnosis model 4430 extracted at S7100 to the diagnosis model 3470 in the non-volatile memory 3300. The loading enables the machine 1010 to examine sensor data with the latest diagnosis model 3470.

At S7400, the diagnosis model update program 3460 stores a value VALID in the diagnosis model lacking flag data 3370 to indicate that the diagnosis model is lacking. The value VALID stored in the diagnosis model lacking flag data 3370 leads the examined machine 1010 to have the data center 1130 create a diagnosis model or examine sensor data in later-described processing.

After S7300 or S7400, the diagnosis model update program 3460 updates the last update day data 3375 with the date of the current day (S7500). The last update day data 3375 updated with the current date enables the examined machine 1010 to determine whether to update the diagnosis model at S6015.

After S7500, the diagnosis model update program 3460 terminates the processing shown in FIG. 19.

After S6015 or S6020, the examined machine 1010 refers to the next connection day data 3350 and determines whether the current day is the day for the next connection to the data center 1130 (S6025).

If the current day is the day for the next connection to the data center 1130 or if the current day is later than the day for the next connection to the data center 1130, the examined machine 1010 proceeds to S6030 to connect to the data center 1130. If the current day is prior to the day for the next connection to the data center 1130, the examined machine 1010 proceeds to S6035 because it does not have to connect to the data center 1130.

At S6030, the examined machine 1010 connects to the data center 1130 in accordance with a later-described subroutine SUB1. At S6030, the examined machine 1010 sends sensor data to the data center 1130 and receives diagnosis models from the data center 1130.

Figure 20:
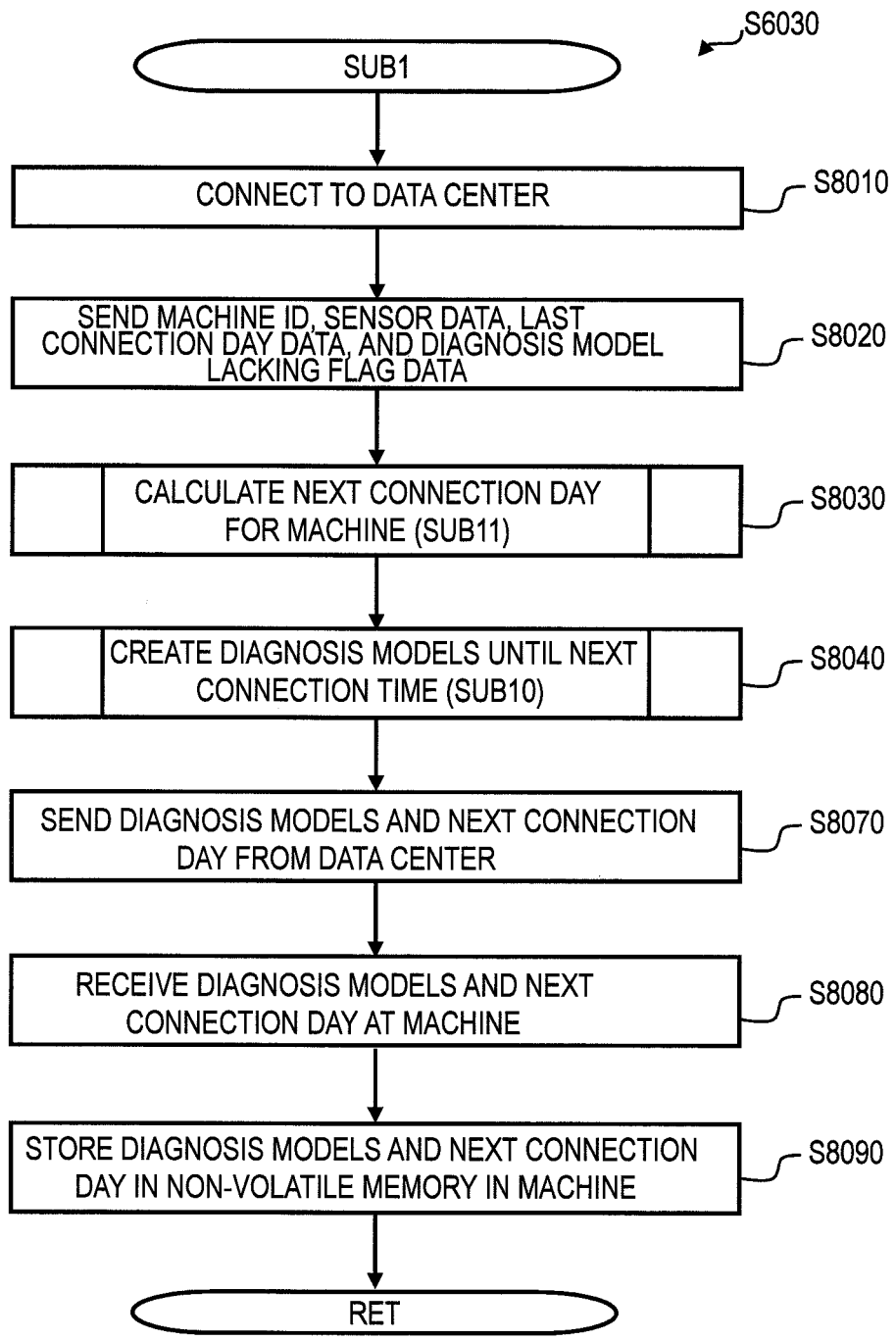
FIG. 20 is a flowchart illustrating processing of a subroutine SUB1 in the embodiment.

FIG. 20 is a flowchart illustrating processing of the subroutine SUB1 in this embodiment.

The processing at S8020, S8080, and S8090 in FIG. 20 is performed by the sensor data transmission program 3440.

The examined machine 1010 connects to the data center 1130 and starts sending and receiving data (S8010).

Specifically at S8010, if the examined machine 1010 is a machine 1020 such as a truck or an excavator, a worker or somebody moves the machine 1020 to the communication point 1100 shown in FIG. 1. Then, the machine 1020 starts communicating data with the data center 1130 via the communication device 1120.

At S8010, if the examined machine 1010 is a stationary machine 1040 such as a power generator, it is difficult for a worker or somebody to move the machine 1040 to the communication point 1100. Accordingly, the maintenance worker 1030 shown in FIG. 1 copies sensor data in the machine 1040 to a storage medium, carries the storage medium including the copy of sensor data to the place of the communication point 1100, and starts communicating data with the data center 1130 at the communication point 1100.

The sensor data transmission program 3440 sends sensor data to the data center 1130 through the communication device 1120. The sensor data to be sent includes at least the identifier of the examined machine 1010 connected to the data center 1130, sensor data, the generation time of the sensor data (or the acquisition time 4100), diagnosis model lacking flag data 3370, and last connection day data 3380 (S8020).

At S8020, the sensor data transmission program 3440 refers to the last connection day data 3380 and extracts the date of the last connection to the data center 1130. It further refers to the acquisition time 4100 and extracts sensor data 4110 of the examined machine 1010 after the day of the last connection to the data center until the current day from the sensor data 4110 held in the machine's sensor table 3330.

Specifically, at S8020, the sensor data transmission program 3440 retrieves the date of the last connection to the data center 1130 extracted from the last connection day data 3380 to the non-volatile memory 3300. It further extracts acquisition times 4100 and pieces of sensor data 4110 after the day of the last connection to the data center 1130 until the current day from the machine's sensor table 3330 and loads the extracted acquisition times 4100 and pieces of sensor data 4110 to the RAM 3400. It further sends the loaded acquisition times and pieces of sensor data to the data center 1130.

At S8020, the sensor data transmission program 3440 also sends the value indicating "VALID" or "INVALID" held in the diagnosis model lacking flag data 3370 to the data center 1130. The examined machine 1010 initially has an identifier uniquely representing itself. Hence, the sensor data transmission program 3440 sends the identifier (ID) of the examined machine 1010 including the program 3440 to the data center 1130.

At S8020, the data center 1130 updates the center's collected sensor tables 3730 with the received sensor data. If the sensor data and others are sent from a new examined machine 1010, the data center also updates the machine sensor configuration table 3710.

It should be noted that the collected working day tables 3760 shown in FIG. 17 may be updated in accordance with the sensor data and the acquisition times of the sensor data received at S8020.

Specifically, the days on which an acquisition time of sensor data does not exist are non-working days; accordingly, the data center 1130 may extract the dates 11700 corresponding to these days on which an acquisition time of sensor data does not exist and store "NON-WORKING DAY" in the states 11600 for the extracted dates 11700. The days on which an acquisition time of sensor data exists are working days; accordingly, the data center 1130 may extract the dates 11700 corresponding to these days on which an acquisition time of sensor data exists and store "WORKING DAY" in the states 11600 for the extracted dates 11700.

After S8020, the data center 1130 calculates the next connection day for the examined machine 1010 (S8030).

At S8030, the data center 1130 calculates the next connection day for the examined machine 1010 in accordance with a subroutine SUB11 described below.

Figure 21:
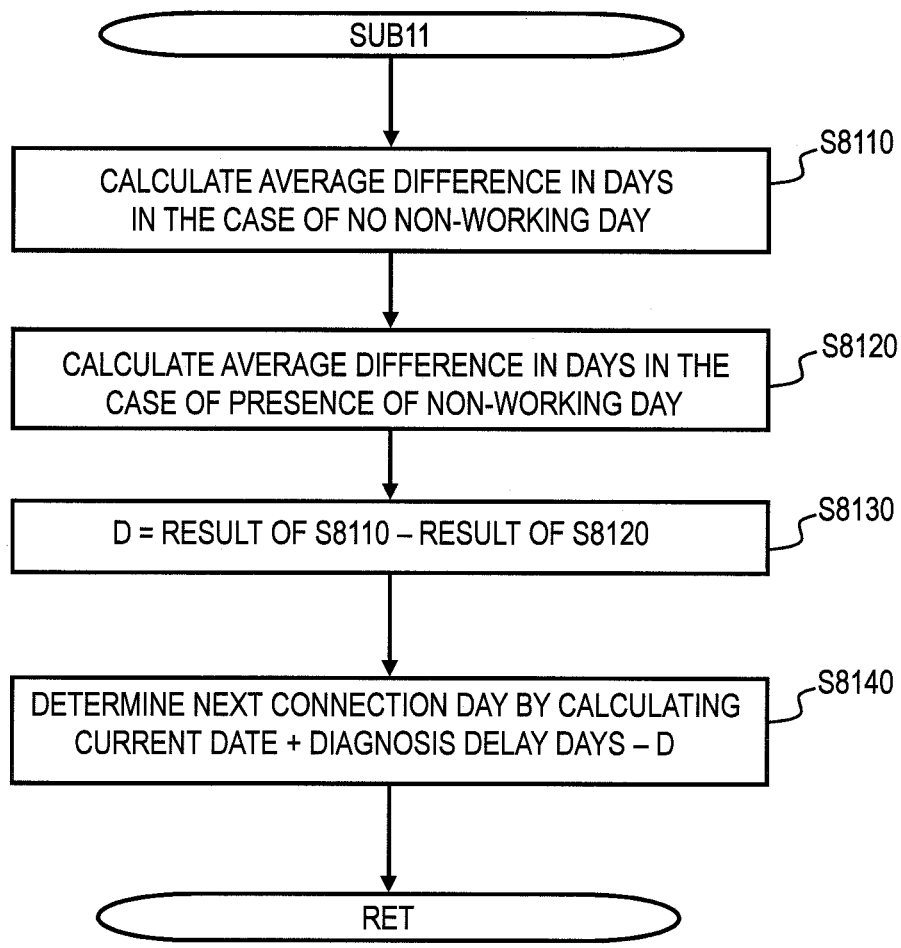
FIG. 21 is a flowchart illustrating processing of a subroutine SUB11 in the embodiment.

FIG. 21 is a flowchart illustrating processing of the subroutine SUB11 in this embodiment.

The next connection day calculation program 3630 held in the data center 1130 calculates an average difference in days between each learning day and a diagnosis day in the case of no non-working day using the foregoing formula (1) during the learning days to learn sensor data (S8110). The data center 1130 holds predetermined learning days.

The data center 1130 has a function to acquire the current date; the current date in the data center 1130 and the current date in the examined machine 1010 are synchronized.

Specifically, assuming that a non-working day does not exist in the period between the current date (the latest day on which the examined machine 1010 is connected to the data center 1130) and the date pushed back by the number of learning days, the next connection day calculation program 3630 calculates the farthest date for the diagnosis day among the dates on which diagnosis can be made with the sensor data sent from the examined machine 1010. The next connection day calculation program 3630 calculates an average difference in days based on the foregoing formula (1) and the obtained farthest diagnosis day.

If the sensor data that can be sent from the examined machine 1010 to the data center 1130 is the one until the day before the day of the latest connection of the examined machine 1010 and the data center 1130, the data center 1130 calculates the farthest date for the diagnosis day, using the sensor data in the period between the latest acquisition time of sensor data and the time pushed back by the number of learning days out of the sensor data received by the data center 1130.

After S8110, the next connection day calculation program 3630 calculates an average difference in days in consideration of non-working days with the foregoing formula (1) (S8120). The next connection day calculation program 3630 extracts non-working days based on the machine working day configuration table 3750 shown in FIG. 16 and the collected working day tables 3760. First, the program 3630 extracts a machine ID 11150 and a working day table name 11170 with the identifier of the examined machine 1010 received at S8020 and extracts a working day table name 11150 corresponding to the extracted working day table name 11170 from the collected working day tables 3760. The program 3630 further extracts non-working days during the learning days with reference to the extracted working day table name 11500.

After S8120, the next connection day calculation program 3630 holds a variable D in the RAM 3600. Then, the next connection day calculation program 3630 stores the number of days obtained by subtracting the average difference in days calculated at S8120 from the average difference in days calculated at S8110 in the variable D (S8130).

The next connection day calculation program 3630 calculates the day for the next connection of the data center 1130 and the examined machine 1010 with the following formula:

$$\text{Next connection day} = \text{Current date} + \text{Diagnosis delay days} - \text{Variable } D \quad (2)$$

It should be noted that, if the sensor data the examined machine 1010 can send to the data center 1130 is the sensor data until the day before the day of the latest connection of the examined machine 1010 and the data center 1130, the data center 1130 calculates the next connection day after changing the current date in the above formula (2) to the acquisition time of the newest sensor data.

The next connection day calculation program 3630 returns the next connection day calculated by the foregoing formula (2) as a return value of the subroutine SUB11 (S8140). Then, the next connection day calculation program 3630 terminates the subroutine SUB 11.

After S8030, the data center 1130 creates diagnosis models for several days until the next connection day by a subroutine SUB10 (S8040).

Figure 22:
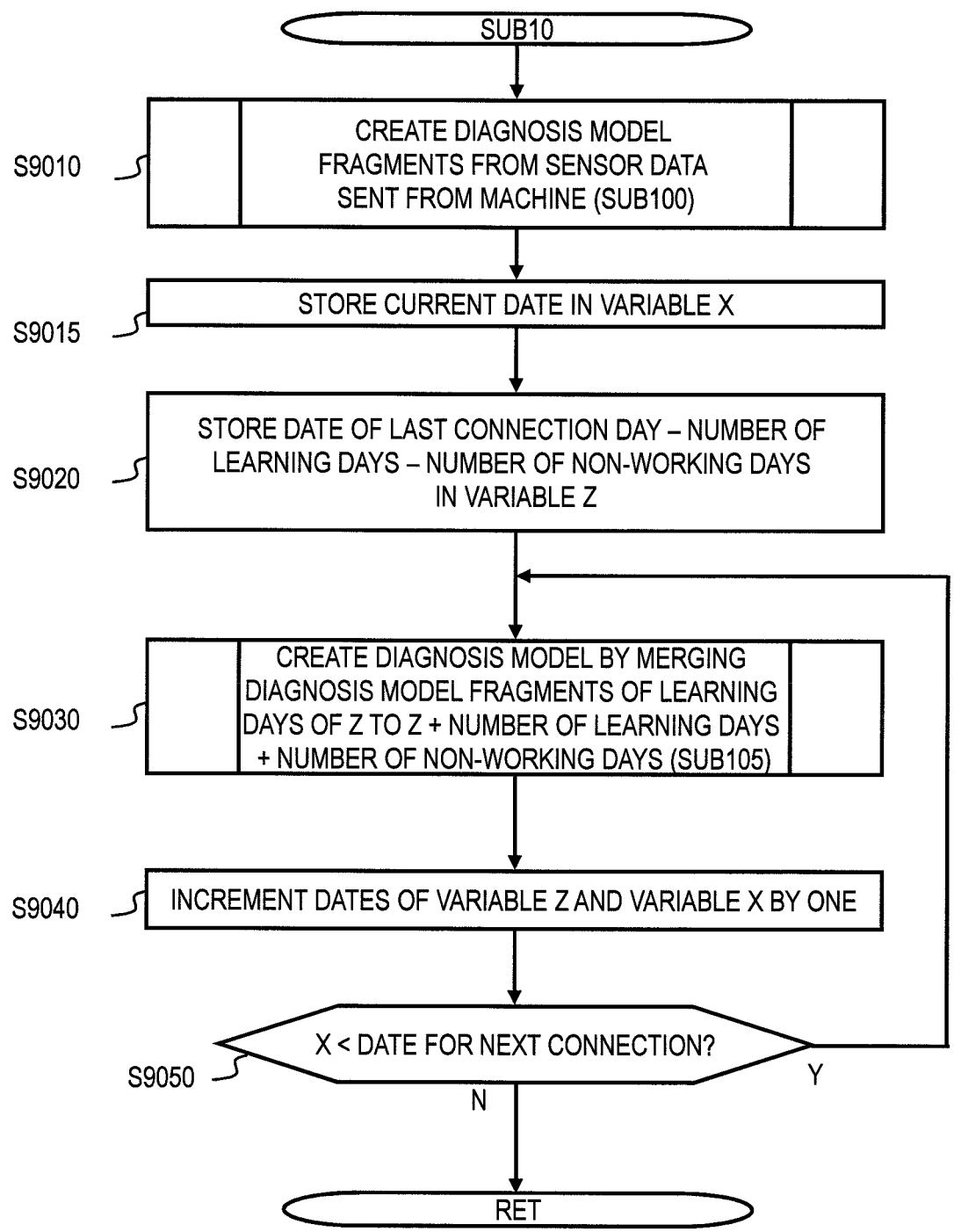
FIG. 22 is a flowchart illustrating processing of a subroutine SUB10 in the embodiment.

FIG. 22 is a flowchart illustrating processing of the subroutine SUB10 in this embodiment.

The data center 1130 first executes a subroutine SUB100 to create diagnosis model fragments based on the sensor data received at S8020 (S9010).

Figure 23:
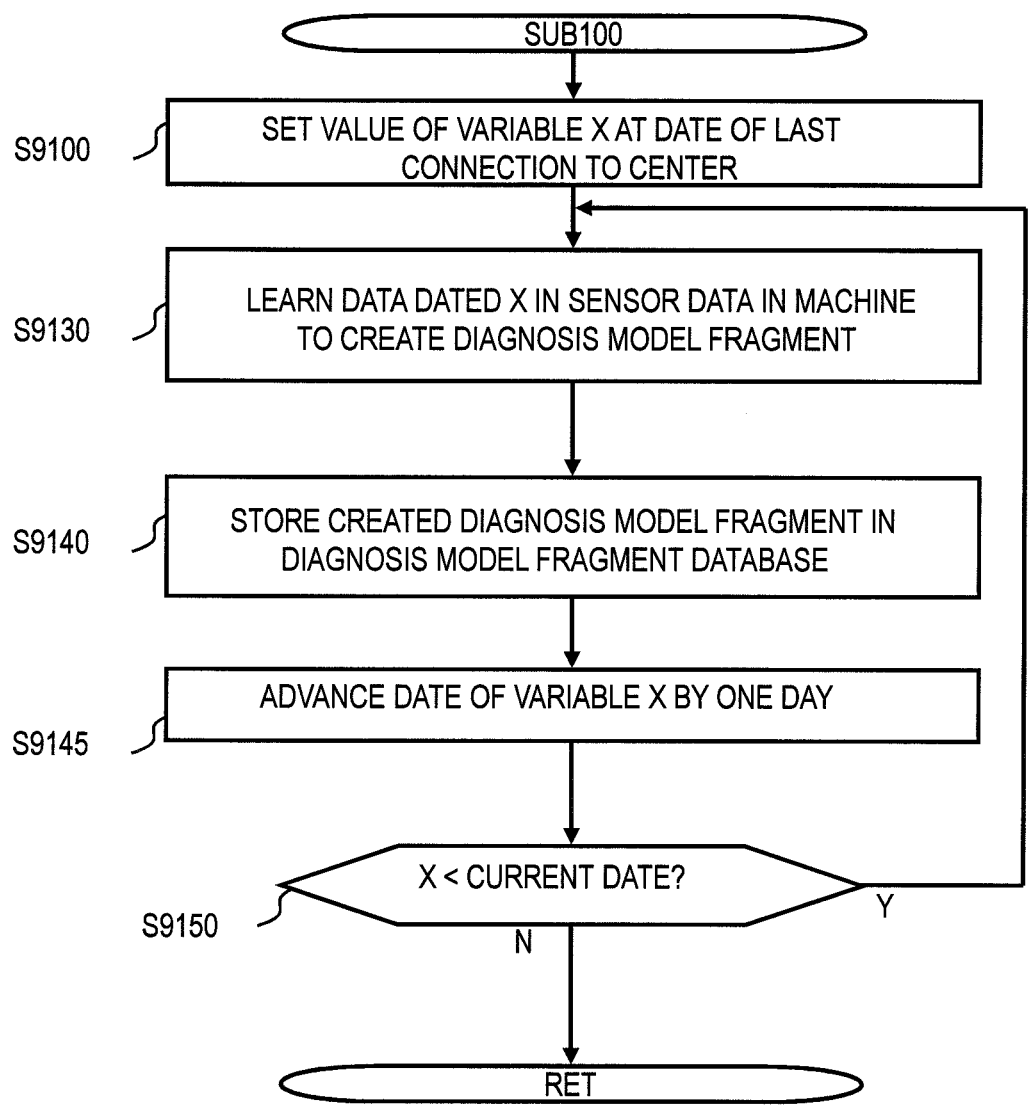
FIG. 23 is a flowchart illustrating processing of a subroutine SUB100 in the embodiment.

FIG. 23 is a flowchart illustrating processing of the subroutine SUB100 in this embodiment.

The diagnosis model fragment search/update program 3640 holds a variable X in the RAM 3600. The program 3640 stores the value indicated by the last connection day data 3380 received at S8020 in the X (S9100).

After S9100, the diagnosis model fragment search/update program 3640 extracts pieces of sensor data for which the acquisition time of the sensor data is X from the sensor data received at S8020. Then, the diagnosis model creation program 3620 learns the extracted pieces of sensor data to create a diagnosis model fragment, which is a diagnosis model for one day (S9130).

After S9130, the diagnosis model fragment search/update program 3640 stores the diagnosis model fragment created at S9130 in the center's collected diagnosis model fragment tables 3740. It stores the value of the variable X in the original data acquisition date 5610 in the center's collected diagnosis model fragment tables 3740 (S9140).

After S9140, the diagnosis model fragment search/update program 3640 advances the date indicated by the variable X by one day by adding one to the value of the variable X (S9145).

Furthermore, the diagnosis model fragment search/update program 3640 determines whether the variable X indicates a date prior to the current date (S9150). If the variable X indicates a date prior to the current date, the diagnosis model fragment search/update program 3640 returns to S9130. If not, the program 3640 terminates the subroutine SUB100. At the termination, the data center 1130 releases the variable X held in the RAM 3600.

After S9010, the data center 1130 holds a new variable X in the RAM 3600 and stores the date indicated by the last connection day data in the variable X (S9015).

After S9015, the data center 1130 holds a variable Z in the RAM 3600. The data center 1130 calculates the date of "the last connection day–the number of learning days–the number of non-working days during the learning days" and stores the obtained date in the variable Z (S9020). The data center 1130 can calculate the first day of the learning days by S9020.

The data center 1130 extracts "the number of non-working days during the learning days" based on the machine working day configuration table 3750 and the collected working day tables 3760. Specifically, it extracts a machine ID 11150 and a working day table name 11170 from the machine working day configuration table 3750 and extracts non-working days during the learning days from the collected working day tables 3760 with the extracted 11170.

After S9020, the data center 1130 executes a subroutine SUB105 using the variables X and Z as parameters to merge diagnosis model fragments of the working days (S9030). In the subroutine SUB105, the variable X represents the diagnosis day and the variable Z represents the first day of the learning days.

Figure 24:
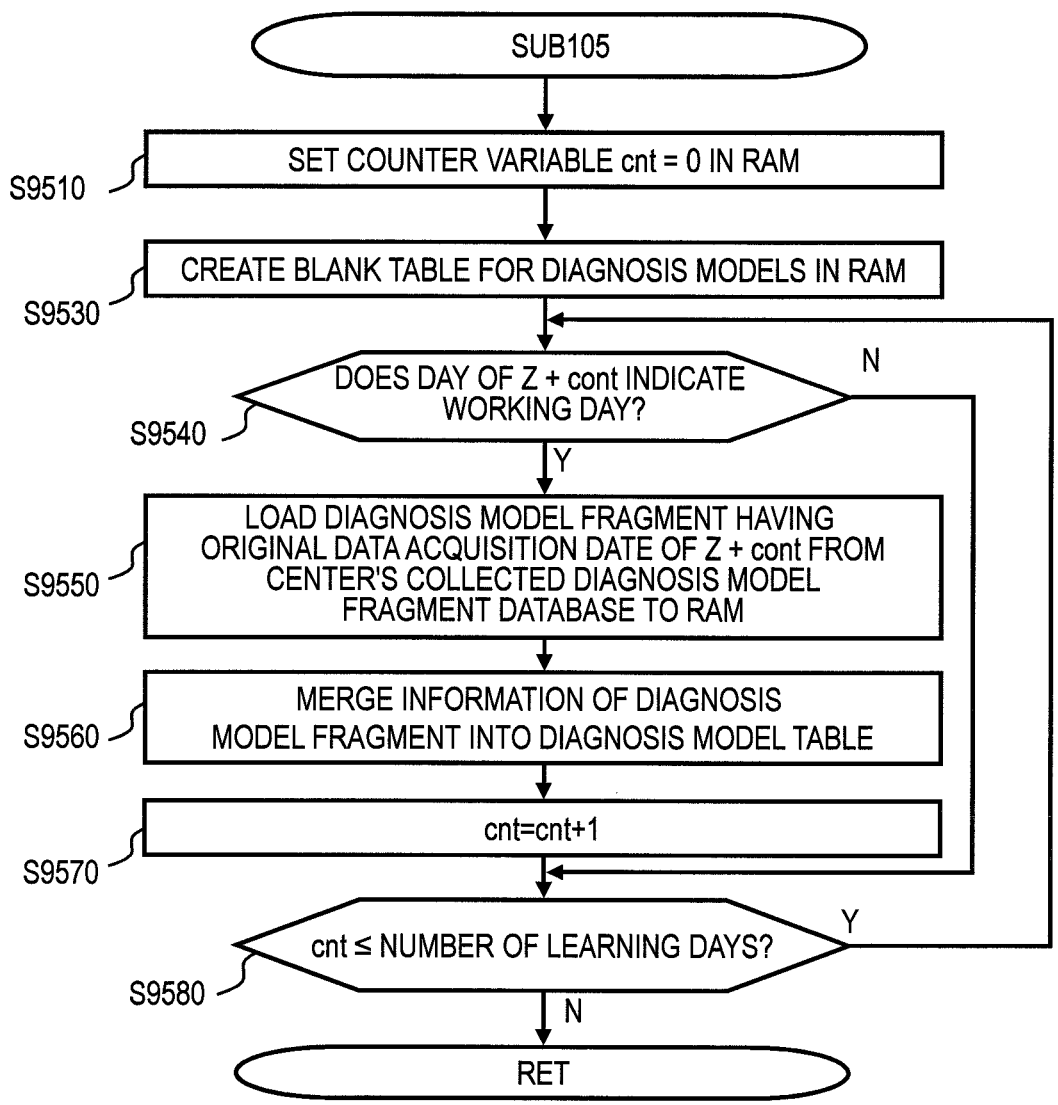
FIG. 24 is an explanatory diagram illustrating processing of a subroutine SUB105 in the embodiment.

FIG. 24 is an explanatory diagram illustrating the processing of the subroutine SUB105 in this embodiment.

The diagnosis model fragment merging program holds a count variable cnt in the RAM 3600 to count learning days and stores an initial value 0 in the count variable cnt (S9510).

After S9510, the diagnosis model fragment merging program holds a memory to store merged diagnosis model fragments, or diagnosis models, in the RAM 3600 (S9530).

FIG. 25 is an explanatory diagram illustrating a table 14000 for holding diagnosis models in the RAM 3600 in this embodiment.

The table 14000 stores the data structure of diagnosis models. The table 14000 includes diagnosis days 14100, the centers of normal ranges 14200, and the radii of normal ranges 14300. In the diagnosis days 14100, diagnosis days to use the diagnosis model fragments are stored.

The centers of normal ranges 14200 and the radii of normal ranges 14300 correspond to the centers of normal ranges 4433 and the radii of normal ranges 4436, respectively, in the diagnosis models 4430.

At S9530, the table 14000 held in the RAM 3600 does not have any value.

After S9530, the diagnosis model fragment merging program sums the variable Z given as a parameter and the count variable cnt, and determines whether the obtained value indicates a working day with reference to the collected working day tables 3760 (S9540).

If the value obtained by summing the variable Z and the count variable cnt indicates a working day, a diagnosis model fragment can be extracted; accordingly, the diagnosis model fragment merging program proceeds to S9550. If the value obtained by summing the variable Z and the count variable cnt indicates a non-working day, a diagnosis model fragment cannot be extracted; accordingly, the diagnosis model fragment merging program proceeds to S9580.

After S9540, the diagnosis model fragment merging program extracts a diagnosis model fragment 5640 for which the date indicated by the value obtained by summing the variable Z and the count variable cnt matches with an original data acquisition date 5610 from the center's collected diagnosis model fragment tables 3740 and loads the extracted diagnosis model fragment 5640 to the RAM 3600 (S9550).

After S9550, the diagnosis model fragment merging program adds the diagnosis model fragment 5640 loaded to the RAM 3600 to the table 14000. The program stores the date indicated by the variable X given as a parameter in the diagnosis day 14100. Then, it stores the centers of normal ranges 5643 of the extracted diagnosis model fragment 5640 in the centers of normal ranges 14200 and the radii of normal ranges 5646 in the radii of normal ranges 14300 (S9560).

At S9560, if values of the variable X are the same, the diagnosis model fragment merging program adds the centers of normal ranges and the radii of normal ranges in the row of the same diagnosis day 14100. This means that the program merges diagnosis model fragments by adding the centers of normal ranges and the radii of normal ranges in the row of the same diagnosis day 14100.

After S9560, the diagnosis model fragment merging program increments the count variable cnt by one (S9570). The count variable cnt+1 enables extraction of all the diagnosis model fragments on the learning days for creating a diagnosis model. In other words, the subroutine SUB105 can be terminated after diagnosis model fragments 5640 are extracted for all learning days.

After S9530 or S9570, the diagnosis model fragment merging program determines whether the count variable cnt is equal to or smaller than the predetermined number of learning days (S9580). If the count variable cnt is equal to or smaller than the predetermined number of learning days, the program returns to S9540 to further extract a diagnosis model fragment 5640.

If the count variable cnt is greater than the predetermined number of learning days, the diagnosis model fragment merging program terminates the subroutine SUB105 since it does not have to further extract a diagnosis model fragment 5640.

After S9030, the data center 1130 adds one to the variable X and shifts the date indicated by the variable X to the future by one day (S9040). This operation enables creation of a diagnosis model after the last time the examined machine 1010 is connected to the data center 1130 until the next connection day.

After S9040, the data center 1130 determines whether the date indicated by the variable X indicates a date prior to the next connection day calculated at S8030 (S9050). If the variable X indicates a date prior to the next connection day, all diagnosis models have not been created; the data center returns to S9030. If the variable X indicates either the next connection day or a later date, it terminates the subroutine SUB10.

After S8040, the data center 1130 sends the diagnosis models in the table 14000 created at S8040 and the next connection day calculated at S8030 to the examined machine 1010 (S8070). It should be noted that the diagnosis day to use the diagnosis model is attached to each diagnosis model.

After S8070, the examined machine 1010 receives the diagnosis models and the next connection day from the data center 1130 (S8080).

After S8080, the examined machine 1010 adds the diagnosis models and the next connection day received at S8080 to the machine's diagnosis model table 3360 (S8090). Specifically, the examined machine 1010 stores values in the table 14000 to the machine's diagnosis model table 3360: the diagnosis days 14100 in the table 14000 to the diagnosis days 4420, the centers of normal ranges 14200 in the table 14000 to the centers of normal ranges 4433 in each diagnosis model 4430, and the radii of normal ranges 14300 in the table 14000 to the radii of normal ranges 4436 in each diagnosis model 4430.

Furthermore, the examined machine 1010 updates the next connection day data 3350 with the received next connection day.

After S8090, the examined machine 1010 terminates the processing of the subroutine SUB1. Namely, the examined machine 1010 terminates the processing of S6030.

After S6025, S6030, or later-described S6140, a worker operates the examined machine 1010 at the working site 1000 (S6035). At S6035, the maintenance worker 1030 allows the examined machine 1010 to perform regular functions held in the examined machine 1010. For example, if the examined machine 1010 is a loader, the maintenance worker 1030 allows the examined machine 1010 to carry soil. At S6035, the sensors 3100 in the examined machine 1010 measure the conditions of individual parts of the examined machine 1010 and generate sensor data with the results of measurement.

After S6035, the examined machine 1010 collects sensor data, which is the results of measurement by the sensors 3100 at S6035, with the sensor controller 3120. It stores the collected sensor data in sensor data 4110 together with an acquisition time 4100 in the non-volatile memory 3300 (S6040).

An optimum interval to collect sensor data is predetermined depending on the method of making diagnosis, the kind of examined machine 1010, the size of the memory, and the like. Accordingly, S6035 and S6040 may be repeated with the predetermined interval. S6035 and S6040 may be performed concurrently.

After S6040, the examined machine 1010 diagnoses whether the examined machine 1010 is abnormal or not and whether any sign of failure exists or not in the examined machine 1010 based on the sensor data 4110 collected at S6040 (S6050).

Specifically, at S6040, the examined machine 1010 extracts a diagnosis model 4430 for which the diagnosis day 4420 in the machine's diagnosis model table 3360 indicates the current date. If the value of the sensor data 4110 collected at S6040 is included in the circular areas of the normal ranges indicated by the centers of normal ranges 4433 and the radii of normal ranges 4436 in the extracted diagnosis model 4430, the examined machine 1010 diagnoses the examined machine 1010 as normal. If the value of the sensor data 4110 collected at S6040 is not included in the circular areas of the normal ranges, the examined machine 1010 diagnoses the examined machine 1010 as abnormal or diagnoses that a sign of failure exists in the examined machine 1010.

After S6050, the examined machine 1010 determines whether the examined machine 1010 has been diagnosed as abnormal or whether a sign of failure exists in the examined machine 1010 at S6050 (S6060). If the diagnosis indicates existence of an abnormality or a sign of failure, the examined machine 1010 proceeds to S6070 to notify the maintenance worker 1030 of the occurrence of abnormality. If the diagnosis does not indicate existence of an abnormality or a sign of failure, the examined machine 1010 returns to S6035 to continue measurement by the sensors 3100.

After S6060, the examined machine 1010 notifies the worker or the maintenance worker 1030 of the examined machine 1010 of the occurrence of an abnormality via the machine's indicator 3180. The examined machine 1010 stops operation of regular functions held in the examined machine 1010 (S6070).

After S6070, the examined machine 1010 is connected to the data center 1130 and sends sensor data 4110 and the diagnosis model lacking flag data 3770 to the data center 1130. Alternatively, the maintenance worker 1030 sends the sensor data 4110, the diagnosis model lacking flag data 3770, and a notification indicating that the examined machine 1010 is diagnosed as abnormal to the data center 1130 via a storage medium. The examined machine 1010 sends the sensor data 4110 after the last connection day until the current date to the data center 1130 (S6080). At S6080, the data center 1130 stores the transmitted sensor data 4110 in the center's collected sensor tables 3730.

After S6080, the data center 1130 refers to the diagnosis model lacking flag data 3370 received at S6080 and determines whether the value indicated by the diagnosis model lacking flag data 3370 is "VALID" (S6100). If the value indicated by the diagnosis model lacking flag data 3370 is not "VALID", the diagnosis by the examined machine 1010 is accurate since the examined machine 1010 has made a diagnosis in accordance with a sufficient diagnosis model. Accordingly, the data center 1130 proceeds to S6160.

If the value indicated by the diagnosis model lacking flag data 3370 is "VALID", the diagnosis might be inaccurate since the diagnosis models held by the examined machine 1010 is insufficient. Accordingly, the data center 1130 proceeds to S6120 to reexamine the machine 1010.

After S6100, the data center 1130 creates a diagnosis model through the above-described subroutine SUB10 in order to reexamine the sensor data sent from the examined machine 1010. Then, the data center 1130 diagnoses whether the examined machine 1010 is abnormal or whether any sign of failure exists in the examined machine 1010 with the created diagnosis model and the sensor data sent at S6080 (S6120).

At S6120, the data center 1130 diagnoses again whether the examined machine 1010 is abnormal using the center's collected sensor tables 3730 and the table 14000, as the examined machine 1010 has done at S6050. Furthermore, the data center 1130 sends the diagnosis to the examined machine 1010.

It should be noted that, at S6120, the data center 1130 may create a diagnosis model for which the diagnosis day (namely, the variable X) is the current date. The data center 1130 may send the created diagnosis model to the examined machine 1010 to let it make an examination. Additionally, the examined machine 1010 may send the diagnosis to the data center 1130.

After S6120, the data center 1130 determines whether it has been diagnosed again that an abnormality or a sign of failure exists in the examined machine 1010 at S6120 (S6140). If it has been diagnosed again that an abnormality or a sign of failure exists in the examined machine 1010, the diagnosis by the examined machine 1010 is accurate; accordingly, the data center proceeds to S6160.

If it is diagnosed that an abnormality or a sign of failure does not exist in the examined machine 1010, the data center 1130 determines that the examined machine 1010 has made a wrong diagnosis because the diagnosis model held in the examined machine 1010 is old. The data center 1130 notifies the examined machine 1010 that the diagnosis is wrong; the examined machine 1010 returns to S6035.

After S6100 or S6140, the data center 1130 sends a notice indicating that an abnormality or a sign of failure exists in the examined machine 1010 to a maintenance worker working for the maintenance service company (S6160). Upon receipt of the notice from the data center 1130, the maintenance service company server 3920 in the maintenance service company 1140 makes a maintenance worker check the notice with the maintenance service company's indicator 3940.

In this embodiment, an examined machine 1010 working at a remote place is connected to the data center 1130 after a certain period to send sensor data and receive diagnosis models. Consequently, the examined machine 1010 can diagnose whether the machine 1010 itself is abnormal or whether any sign of failure exists in the machine 1010 even if the examined machine 1010 is not always connected to the data center 1130.

In addition, the examined machine 1010 does not need to connect to the data center 1130 every day; less expense is achieved for the maintenance of the examined machine 1010.

After an abnormality is detected by the examined machine 1010, the data center 1130 recreates a latest diagnosis model and makes a reexamination for any abnormality, so that more accurate examination for abnormality is available.

Furthermore, in creating a diagnosis model, the data center 1130 in this embodiment uses sensor data of working days of the examined machine 1010 and does not include non-working days of the examined machine 1010 in learning days. As a result, a more accurate diagnosis model can be created.

As set forth above, this invention has been described in details with reference to the accompanying drawings; however, this invention is not limited to these specific configurations but includes various modifications and equivalent configurations within the scope of the appended claims.

This invention is applicable to a system for making examination for any abnormality or sign of failure in a machine in need of maintenance or a machine to be maintained.

What is claimed is:

1. A sensor system comprising:
a machine including sensors; and
a computer connected to the machine via a network,
wherein the machine is configured to:
measure conditions of parts in the machine with the sensors;
collect pieces of sensor data generated by the measurements, including pieces of sensor data for at least one day; and
transmit the collected pieces of sensor data, including the pieces of sensor data in the at least one day, to the computer while connecting to the computer via the network,
wherein the computer is configured to:
hold the transmitted pieces of sensor data in at least one day for respective dates of generation of sensor data in the machine;
create a first index for indicating that the machine is in a predetermined condition, based on the transmitted pieces of sensor data;
transmit the created first index to the machine;
create first indices each for indicating that the machine is in the predetermined condition, for the respective dates of generation of sensor data, based on the pieces of sensor data held in the computer;
determine a diagnosis date to diagnose whether the machine is in the predetermined condition;
calculate a first period associated with the diagnosis date based on the determined diagnosis date and a first predetermined number of days;
create a second index including the first indices in the calculated first period; and
transmit the created second index and the determined diagnosis date to the machine, and
wherein the machine is configured to diagnose whether the machine is in the predetermined condition with the transmitted index and collected pieces of sensor data and wherein the machine is configured to diagnose whether the machine is in the predetermined condition with the transmitted second index and collected pieces of sensor data on the transmitted diagnosis date.

2. The sensor system according to claim 1,
wherein the machine is configured to transmit the collected pieces of sensor data in at least one day to the computer on a connection date to connect to the computer,
wherein the computer is configured to:
calculate a first diagnosis date by summing the connection date and a second predetermined number of days; and
calculate a next connection date for the machine to transmit pieces of sensor data to the computer, based on the calculated first diagnosis date.

3. The sensor system according to claim 2,
wherein the computer is configured to:
extract dates of the first predetermined number of days continuous to the connection date;
subtract each of the extracted dates individually from the calculated first diagnosis date;
calculate a first average difference in days by dividing a sum of results of the subtractions by the first predetermined number of days;
extract dates of the first predetermined number of days, in an order from the latest date to the earliest date, from the dates on which the pieces of sensor data transmitted from the machine are generated by the connection date;
subtract each date of the extracted first predetermined number of days individually from the calculated first diagnosis date;
calculate a second average difference in days by dividing a sum of results of the subtractions by the first predetermined number of days; and
calculate a second diagnosis date by subtracting a result of subtracting the first average difference in days from the second average difference in days from the first diagnosis date.

4. The sensor system according to claim 3,
wherein the machine is configured to transmit pieces of sensor data to the computer in a case where the machine has diagnosed that the machine is in the predetermined condition, and wherein the computer is configured to:
  diagnose whether the machine is in the predetermined condition with a created index and the transmitted pieces of sensor data; and
  generate data to report that the machine is in the predetermined condition in a case where the computer has diagnosed that the machine is in the predetermined condition.

5. A computer to be connected to a machine including sensors via a network, the computer being configured to:
  receive pieces of sensor data generated in the machine from the machine, including pieces of sensor data for at least one day;
  create an index for indicating that the machine is in a predetermined condition, based on the received pieces of sensor data;
  transmit the created index to the machine for the machine to diagnose whether the machine is in the predetermined condition;
  hold the received pieces of sensor data in at least one day for respective dates of generation of sensor data in the machine;
  create first indices each for indicating that the machine is in the predetermined condition, for the respective dates of generation of sensor data, based on the pieces of sensor data held in the computer;
  determine a diagnosis date to diagnose whether the machine is in the predetermined condition;
  calculate a first period associated with the diagnosis date based on the determined diagnosis date and a first predetermined number of days;
  create a second index including the first indices in the calculated first period; and
  transmit the created second index and the determined diagnosis date to the machine.

6. The computer according to claim 5, further configured to:
  receive the pieces of sensor data in at least one day on a connection date to connect to the computer;
  calculate a first diagnosis date by summing the connection date and a second predetermined number of days; and
  calculate a next connection date for the machine to transmit pieces of sensor data to the computer, based on the calculated first diagnosis date.

7. The computer according to claim 6, further configured to:
  extract dates of the first predetermined number of days continuous to the connection date; subtract each of the extracted dates individually from the calculated first diagnosis date;
  calculate a first average difference in days by dividing a sum of results of the subtractions by the first predetermined number of days;
  extract dates of the first predetermined number of days, in an order from the latest date to the earliest date, from the dates on which the pieces of sensor data transmitted from the machine are generated by the connection date;
  subtract each date of the extracted first predetermined number of days individually from the calculated first diagnosis date;
  calculate a second average difference in days by dividing a sum of results of the subtractions by the first predetermined number of days; and
  calculate a second diagnosis date by subtracting a result of subtracting the first average difference in days from the second average difference in days from the first diagnosis date.

8. The computer according to claim 7,
wherein in a case where the machine has diagnosed that the machine is in the predetermined condition, the computer is further configured to:
receive pieces of sensor data from the machine;
diagnose whether the machine is in the predetermined condition with a created index and the transmitted pieces of sensor data; and
generate data to report that the machine is in the predetermined condition in a case where the computer has diagnosed that the machine is in the predetermined condition.

* * * * *